US011883261B2

(12) United States Patent
Coulthard et al.

(10) Patent No.: US 11,883,261 B2
(45) Date of Patent: Jan. 30, 2024

(54) MEDICAL DRESSING FULL INDICATOR

(71) Applicant: KCI Licensing, Inc., San Antonio, TX (US)

(72) Inventors: Richard Daniel John Coulthard, Verwood (GB); Christopher Brian Locke, Bournemouth (GB)

(73) Assignee: 3M Innovative Properties Company, St. Paul, MN (US)

( * ) Notice: Subject to any disclaimer, the term of this patent is extended or adjusted under 35 U.S.C. 154(b) by 1194 days.

(21) Appl. No.: 16/315,995

(22) PCT Filed: Jun. 1, 2017

(86) PCT No.: PCT/US2017/035381
§ 371 (c)(1),
(2) Date: Jan. 7, 2019

(87) PCT Pub. No.: WO2018/013242
PCT Pub. Date: Jan. 18, 2018

(65) Prior Publication Data
US 2019/0159939 A1 May 30, 2019

Related U.S. Application Data

(60) Provisional application No. 62/362,475, filed on Jul. 14, 2016.

(51) Int. Cl.
*A61M 1/00* (2006.01)
*A61F 13/00* (2006.01)
(Continued)

(52) U.S. Cl.
CPC .... *A61F 13/00068* (2013.01); *A61F 13/0216* (2013.01); *A61M 1/915* (2021.05);
(Continued)

(58) Field of Classification Search
CPC ............ A61M 1/00; A61M 5/00; A61M 5/32; A61M 25/00; A61M 35/00; A61M 5/178;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Catharine L Anderson
*Assistant Examiner* — Ilya Y Treyger

(57) ABSTRACT

In some illustrative examples, a conduit interface may include a mounting surface and an exterior-facing surface positioned across from the mounting surface, an internal cavity, an inlet port, a vent, and a temporary plug. The internal cavity may include an opening positioned proximate to the mounting surface. The inlet port may be in in fluid communication with the internal cavity through the exterior-facing surface. The vent may be in fluid communication with the internal cavity through the exterior-facing surface. The temporary plug may be configured to temporarily preclude fluid communication through the vent. The conduit interface may be suitable for providing fluid communication with a
(Continued)

dressing at a tissue site. Also provided are other examples, apparatus, systems, and methods.

48 Claims, 10 Drawing Sheets

(51) Int. Cl.
| | |
|---|---|
| *A61F 13/02* | (2006.01) |
| *A61M 5/00* | (2006.01) |
| *A61M 5/32* | (2006.01) |
| *A61M 25/00* | (2006.01) |
| *A61M 35/00* | (2006.01) |
| *A61M 5/178* | (2006.01) |

(52) U.S. Cl.
CPC .............. *A61M 1/964* (2021.05); *A61M 1/784* (2021.05); *A61M 1/985* (2021.05); *A61M 2205/18* (2013.01); *A61M 2205/3382* (2013.01)

(58) Field of Classification Search
CPC ...... A61F 13/00; A61F 7/00; A61F 13/00059; A61F 13/00068; A61F 13/0206; A61F 13/0209; A61F 13/0216; A61F 13/022; A61F 13/0223; A61F 2013/00182
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0225378 A1* | 12/2003 | Wilkie .............. A61B 17/00491 604/221 |
| 2010/0268128 A1 | 10/2010 | Randolph |

(56) References Cited

U.S. PATENT DOCUMENTS

| | | |
|---|---|---|
| 2011/0257572 A1 | 10/2011 | Locke et al. |
| 2014/0121615 A1 | 5/2014 | Locke et al. |
| 2014/0163490 A1 | 6/2014 | Locke et al. |
| 2014/0163491 A1 | 6/2014 | Schuessler et al. |
| 2015/0080788 A1 | 3/2015 | Blott et al. |
| 2015/0119833 A1 | 4/2015 | Coulthard et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2558140 B1 | 6/2016 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philiadelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp . 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Žvadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, The Use of Hypermia in the Postoperative Treatment of Lesions of the Extremities and Thorax, Journal of the American Medical Association 64 (1915), pp. 1548-1549.

Selections from W. Meyer and V. Schmieden, Bier's Hyperemic Treatment in Surgery, Medicine, and the Specialties: A Manual of Its

(56) References Cited

OTHER PUBLICATIONS

Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Extended European Search Report for Corresponding Application No. 20208839.9, dated May 4, 2021.

\* cited by examiner

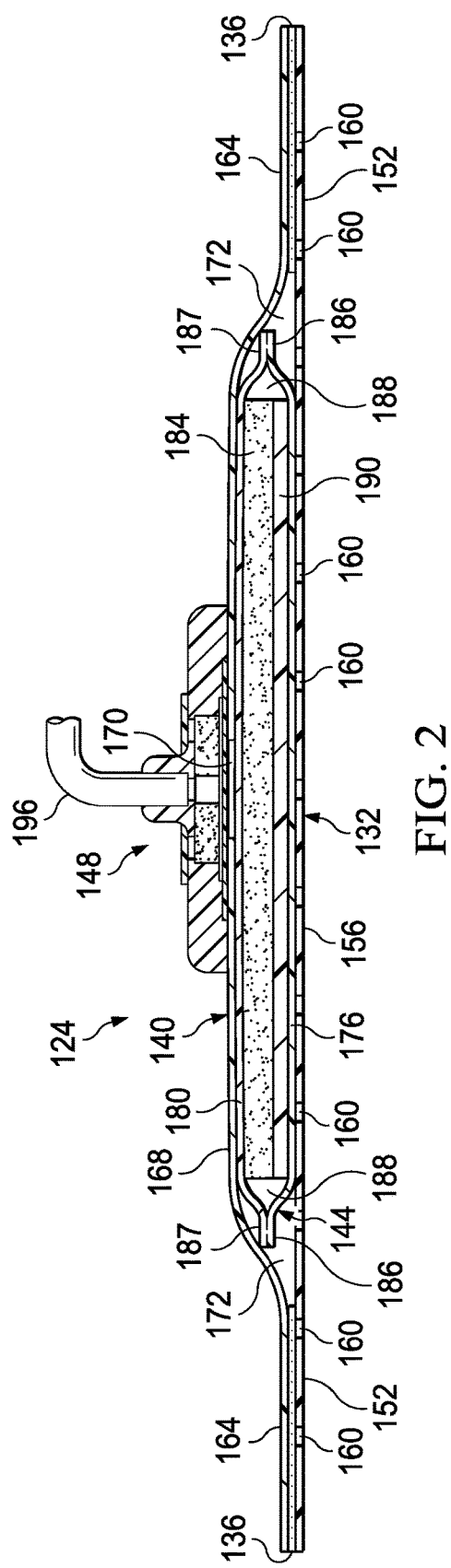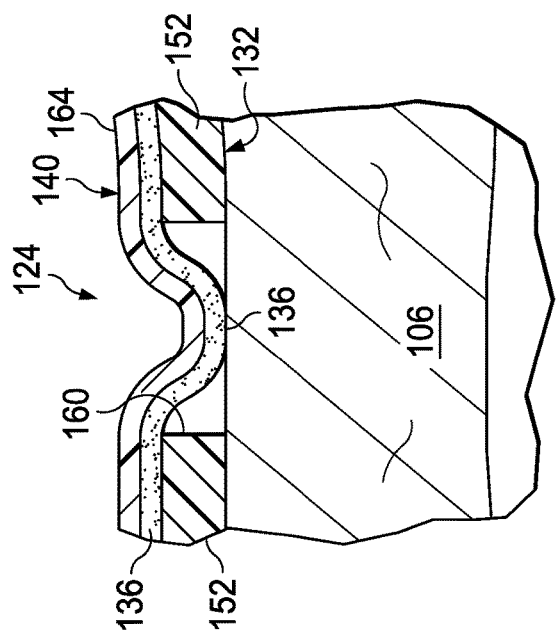

MEDICAL DRESSING FULL INDICATOR

RELATED APPLICATIONS

This application is a U.S. National Phase Entry of International Patent Application No. PCT/US2017/035381, filed Jun. 1, 2017, which claims the benefit, under 35 USC § 119(e), of the filing of U.S. Provisional Patent Application Ser. No. 62/362,475, entitled "Medical Dressing Full Indicator" filed Jul. 14, 2016, which is incorporated herein by reference for all purposes.

TECHNICAL FIELD

This application relates generally to medical treatment systems and, more particularly, but not by way of limitation, to apparatus, dressings, systems, and methods that may be suitable for treating a tissue site.

BACKGROUND

Clinical studies and practice have shown that reducing pressure in proximity to a tissue site can augment and accelerate growth of new tissue at the tissue site. The applications of this phenomenon are numerous, but have been proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "reduced-pressure therapy." However, such treatment may also be known by other names including "negative-pressure therapy," "negative-pressure wound therapy," "vacuum therapy," "vacuum-assisted closure," and "topical negative-pressure," for example. Reduced-pressure therapy may provide a number of benefits, including migration of epithelial and subcutaneous tissues, improved blood flow, and micro-deformation of tissue at a tissue site. Together, these benefits can increase development of granulation tissue and reduce healing times. Improvements to therapy systems, components, and processes may benefit manufacturers, healthcare providers, and patients.

SUMMARY

In some illustrative, non-limiting examples, a dressing may include a sealing member, an inlet port, a vent, and a transformable plug. The sealing member may be configured to provide a sealed space at the tissue site. The inlet port may be configured to be in fluid communication with the sealed space. The vent may be configured to be in fluid communication between the sealed space and an atmosphere exterior to the sealed space. The transformable plug may be configured to change from a serviceable state to a deteriorated state. The transformable plug may be configured to preclude fluid communication through the vent in the serviceable state and to permit fluid communication through the vent in the deteriorated state.

In some illustrative, non-limiting examples, a conduit interface may be configured to fluidly communicate with a dressing for treating a tissue site. The conduit interface may include a mounting surface and an exterior-facing surface positioned across from the mounting surface, an internal cavity, an inlet port, a vent, and a temporary plug. The internal cavity may have an opening positioned proximate to the mounting surface. The inlet port may be in fluid communication with the internal cavity through the exterior-facing surface. The vent may be in fluid communication with the internal cavity through the exterior-facing surface. The temporary plug may be configured to temporarily preclude fluid communication through the vent.

In some illustrative, non-limiting examples, a system for treating a tissue site may include a dressing and a reduced pressure source. The dressing may include a sealing member, an absorbent, an inlet port, a vent, a transformable plug, and at least one hydrophobic filter. The sealing member may be configured to cover the tissue site and to provide a sealed space between the sealing member and the tissue site. The absorbent may be configured to be positioned in the sealed space and between the tissue site and the sealing member. The inlet port may be configured to be in fluid communication with the sealed space. The vent may be configured to be in fluid communication between the sealed space and an atmosphere exterior to the sealed space. The transformable plug may be configured to change from a serviceable state to a deteriorated state in response to a liquid saturation level of the absorbent. The transformable plug may be configured to preclude fluid communication through the vent in the serviceable state and to permit fluid communication through the vent in the deteriorated state. The at least one hydrophobic filter may enclose the transformable plug. Further, the at least one hydrophobic filter may be vapor permeable and liquid impermeable. The reduced pressure source may be configured to be coupled in fluid communication with the dressing through the inlet port.

In some illustrative, non-limiting examples, a method for treating a tissue site may include providing a dressing and positioning the dressing to form a sealed space. Further, the method may include venting the sealed space to ambient air exterior to the sealed space when the dressing requires replacement.

In some illustrative, non-limiting examples, a dressing for treating a tissue site may include an inlet port and a valve. The inlet port may be configured to provide fluid communication to the dressing. The valve may be configured to be activated from a closed position to an open position based on a liquid saturation level in the dressing. The valve may be configured to preclude fluid communication to ambient air external to the dressing in the closed position and to permit fluid communication to the ambient air in the open position.

Other aspects, features, and advantages of the illustrative examples will become apparent with reference to the drawings and detailed description that follow.

BRIEF DESCRIPTION OF THE DRAWINGS

FIG. 2 is a cut-away view of the dressing of FIG. 1;

FIG. 3 is detail view taken at reference FIG. 3, shown in FIG. 1, illustrating the dressing of FIG. 1 positioned proximate to tissue surrounding the tissue site;

DETAILED DESCRIPTION OF ILLUSTRATIVE EMBODIMENTS

In the following detailed description of illustrative example embodiments, reference is made to the accompanying drawings that form a part of this disclosure. Other embodiments may be used, and logical, structural, mechanical, electrical, and chemical changes may be made without departing from the scope of this disclosure. Further, the description may omit certain information known to those skilled in the art. Therefore, the following detailed description is non-limiting, and the appended claims define the scope of the illustrative embodiments. Further, as used throughout this disclosure, "or" does not require mutual exclusivity.

Figure 1:
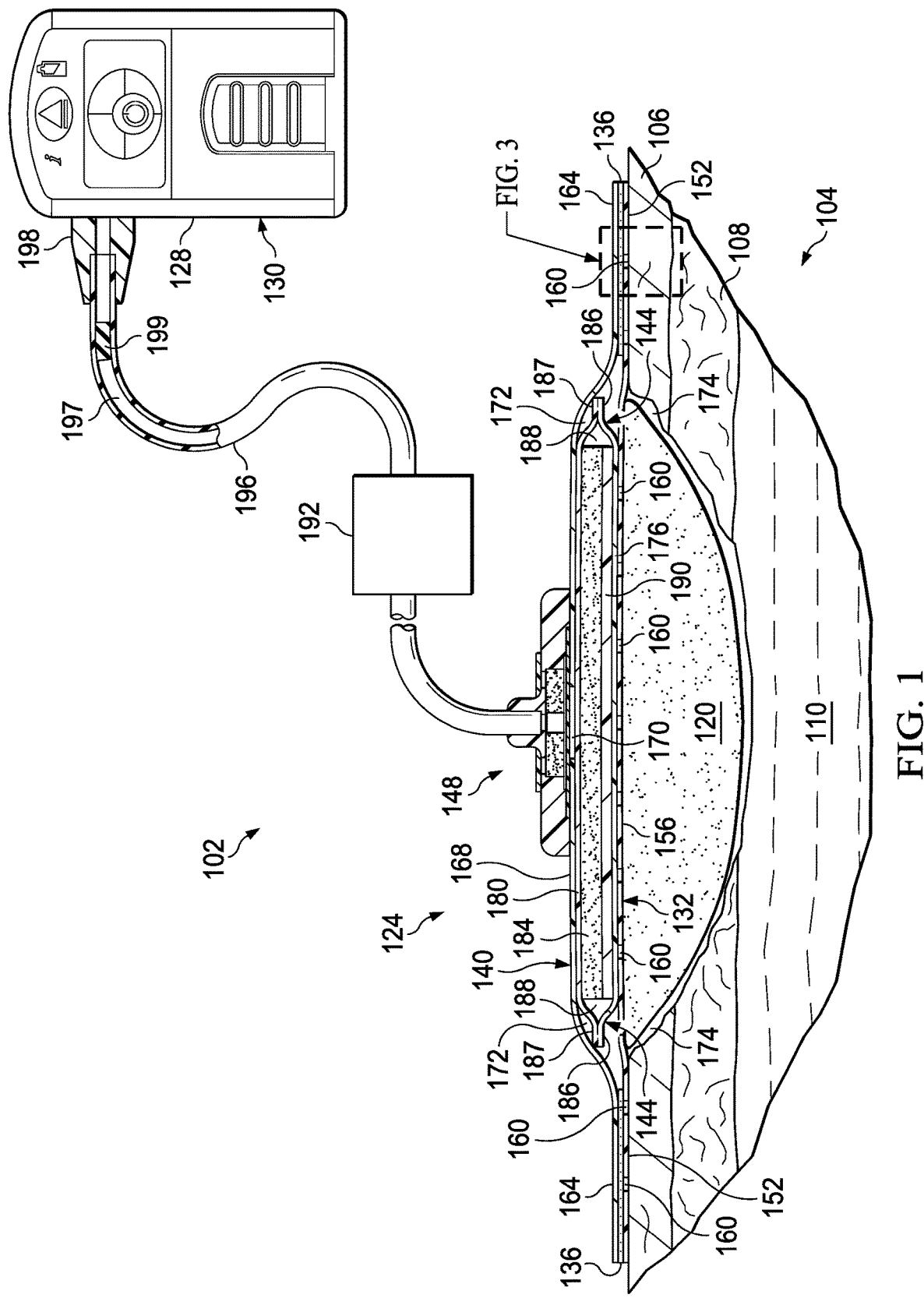
FIG. 1 is a cut-away view of an illustrative example of a system for treating a tissue site depicting an illustrative example of a dressing deployed at the tissue site.
Figure 4A:
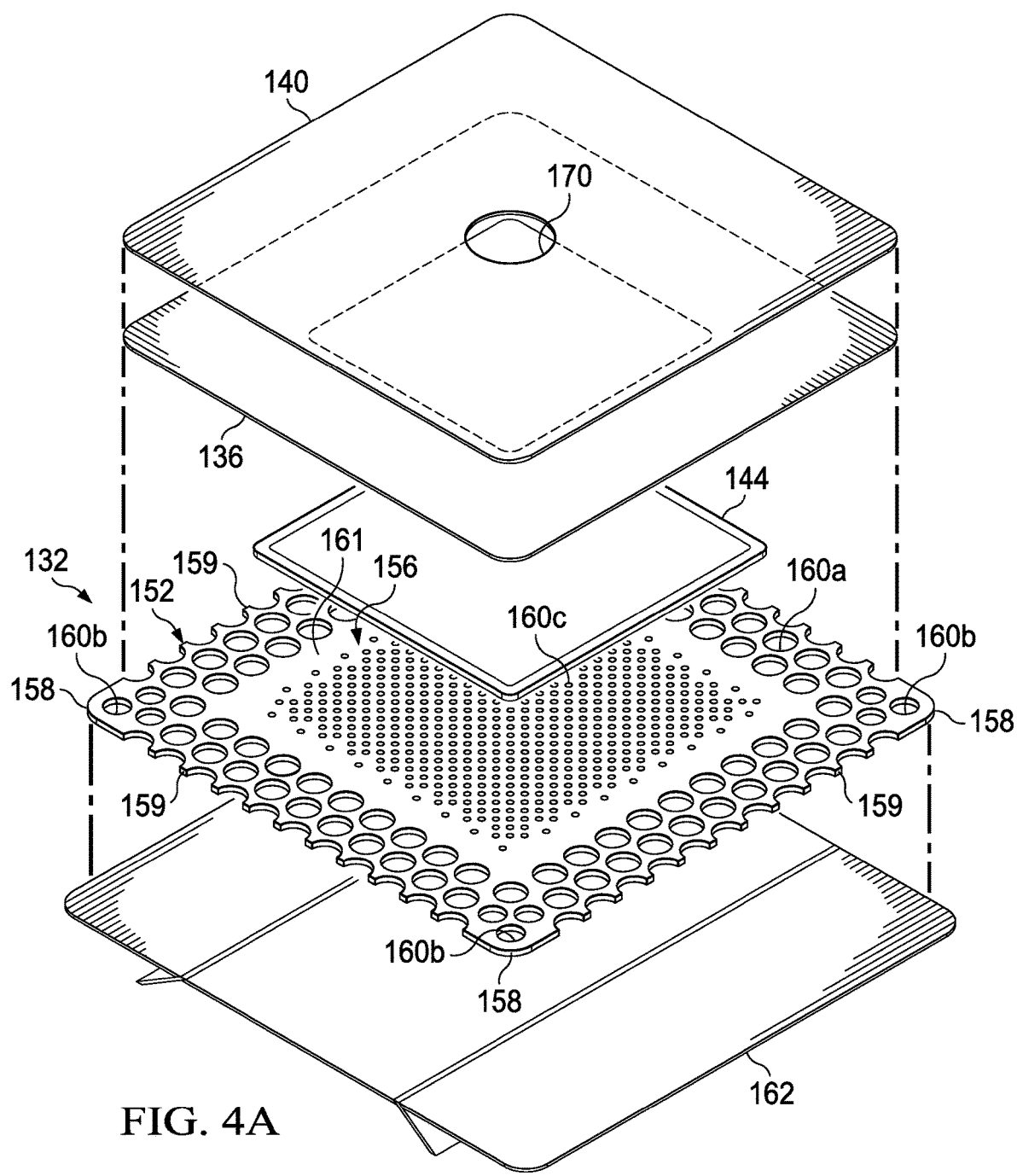
FIG. 4A is an exploded view of the dressing of FIG. 1, depicted without a conduit interface and with an illustrative example of a release liner for protecting the dressing prior to application at the tissue site.
Figure 4B:
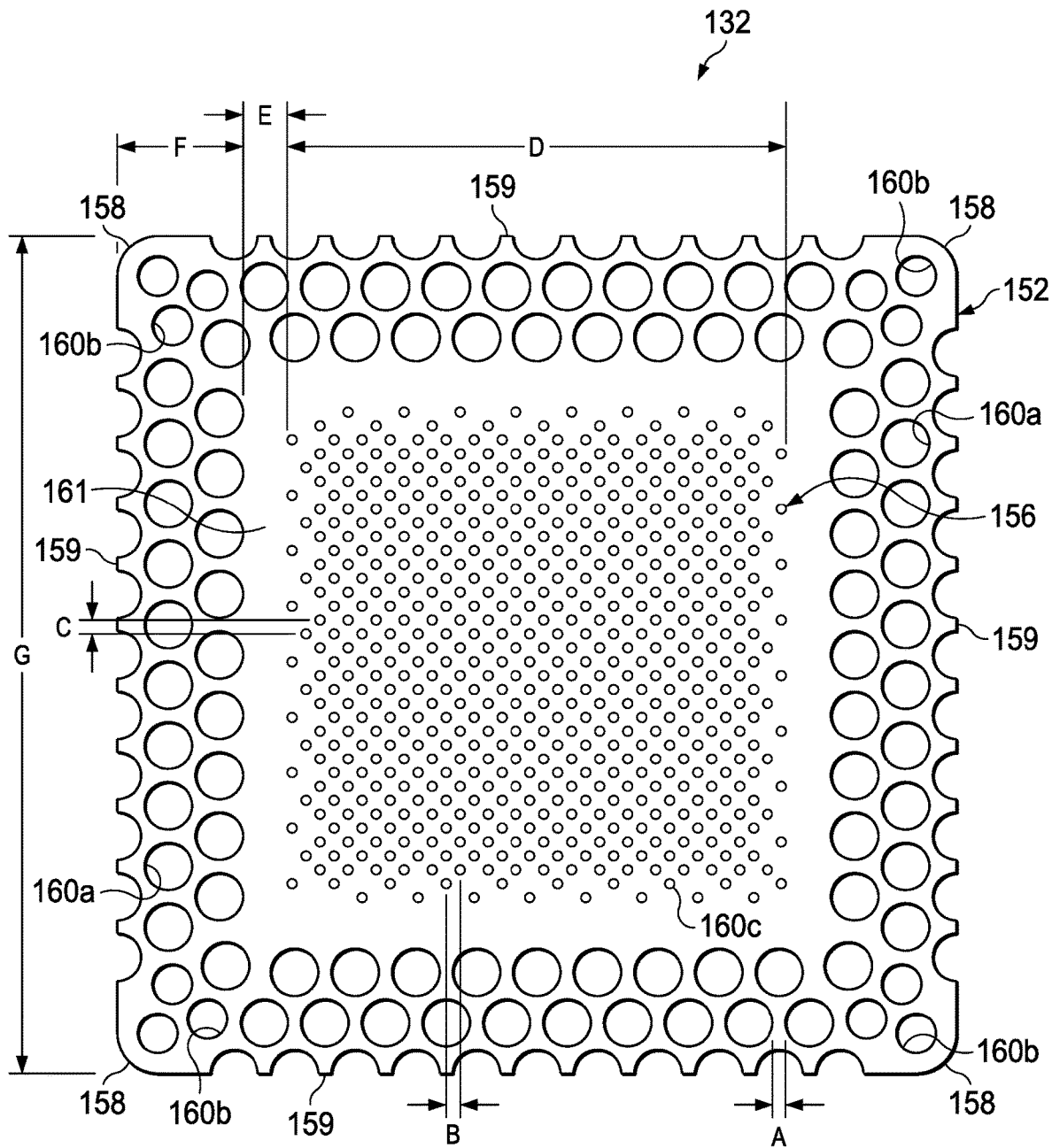
FIG. 4B is a plan view of an illustrative example of a base layer depicted in the dressing of FIG. 4A.

Referring to the drawings, FIG. 1 depicts an illustrative embodiment of a system 102 for treating a tissue site 104 of a patient. The tissue site 104 may extend through or otherwise involve an epidermis 106, a dermis 108, and a subcutaneous tissue 110. The tissue site 104 may be a sub-surface tissue site as depicted in FIG. 1 that may extend below the surface of the epidermis 106. Further, the tissue site 104 may be a surface tissue site (not shown) that may predominantly reside on the surface of the epidermis 106, such as, for example, an incision. The system 102 may provide therapy to, for example, the epidermis 106, the dermis 108, and the subcutaneous tissue 110, regardless of the positioning of the system 102 or the type of tissue site. The system 102 may also be used without limitation at other tissue sites.

The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 104 may include, without limitation, the removal of fluids, such as exudate or ascites, from the tissue site 104, or the delivery of fluids to the tissue site 104. Such treatment may be performed with or without the application or delivery of reduced pressure to the tissue site 104 as described herein.

Continuing with FIG. 1, the system 102 may include an optional tissue interface, such as an interface manifold 120. Further, the system 102 may include a dressing 124 and a reduced-pressure source 128. The reduced-pressure source 128 may be a component of an optional therapy unit 130. In some embodiments, the reduced-pressure source 128 and the therapy unit 130 may be separate components. Further, in some embodiments, the interface manifold 120 may be omitted for different types of tissue sites or different types of therapy, such as, for example, epithelialization. If equipped, the interface manifold 120 may be adapted to be positioned proximate to or adjacent to the tissue site 104, such as, for example, by cutting or otherwise shaping the interface manifold 120 in any suitable manner to fit the tissue site 104. As described below, the interface manifold 120 may be adapted to be positioned in fluid communication with the tissue site 104 to distribute reduced pressure to the tissue site 104 or to communicate fluid to and from the tissue site 104. In some embodiments, the interface manifold 120 may be positioned in direct contact with the tissue site 104.

The tissue interface or the interface manifold 120 may be formed from any manifold material or flexible bolster material that provides a vacuum space, or treatment space, such as, for example, a porous and permeable foam or foam-like material, a member formed with pathways, a graft, or a gauze. In some embodiments, the interface manifold 120 may be a reticulated, open-cell polyurethane or polyether foam that may be fluid permeable while under a reduced pressure. One such foam material is V.A.C.™ GRANUFOAM™ material available from Kinetic Concepts, Inc. (KCI™) of San Antonio, Texas. Further, in some embodiments, any material or combination of materials may be used as a manifold material for the interface manifold 120 provided that the manifold material is operable to distribute or collect fluid. For example, herein the term manifold may refer to a substance or structure configured for delivering fluids to or removing fluids from a tissue site through a plurality of pores, pathways, or flow channels. The plurality of pores, pathways, or flow channels may be interconnected to improve the distribution of fluids provided to and removed from an area around the manifold. Examples of manifolds may include, without limitation, devices that have structural elements arranged to form flow channels, cellular foam, such as open-cell foam, porous tissue collections, and liquids, gels, and foams that include or cure to include flow channels.

In some embodiments, a material with a higher or lower density than GRANUFOAM™ material may be desirable for the interface manifold 120 depending on the application. Among the many possible materials, the following may be used without limitation: GRANUFOAM™ material; FOAMEX™ technical foam (www.foamex.com); a molded bed of nails structure; a patterned grid material, such as those manufactured by Sercol Industrial Fabrics; 3D textiles, such as those manufactured by Baltex of Derby, U.K.; a gauze; a flexible channel-containing member; or a graft. Further, in some embodiments, ionic silver may be added to the interface manifold 120 by, for example, a micro bonding process. Other substances, such as anti-microbial agents, may be added to the interface manifold 120 as well.

In some embodiments, the interface manifold 120 may comprise a porous, hydrophobic material. The hydrophobic characteristics of the interface manifold 120 may prevent the interface manifold 120 from directly absorbing fluid, such as exudate, from the tissue site 104, but allow the fluid to pass through.

In some embodiments, the dressing 124 may include a base layer 132, an adhesive 136, a sealing member 140, a fluid management assembly 144, and a conduit interface 148. However, components of the dressing 124 may be added or removed to suit a particular application or usage. In some embodiments, the dressing 124 may be adapted to provide reduced pressure from the reduced-pressure source 128 to the interface manifold 120, and to extract fluid from the tissue site 104 through the interface manifold 120.

Referring to FIGS. 1-4B, the base layer 132 may have a periphery 152 surrounding a central portion 156, and a plurality of apertures 160 disposed through the periphery 152 and the central portion 156. The base layer 132 may also have corners 158 and edges 159. The corners 158 and the edges 159 may be part of the periphery 152. One of the edges 159 may meet another of the edges 159 to define one of the corners 158. Further, the base layer 132 may have a border 161 substantially surrounding the central portion 156 and positioned between the central portion 156 and the periphery 152. In some embodiments, the border 161 may be free of the apertures 160. In some embodiments, the base layer 132 may be adapted to cover the interface manifold 120 and tissue surrounding the tissue site 104 such that the central portion 156 of the base layer 132 is positioned adjacent to or proximate to the interface manifold 120, and the periphery 152 of the base layer 132 is positioned adjacent to or proximate to tissue surrounding the tissue site 104. In such embodiments, the periphery 152 of the base layer 132 may surround the interface manifold 120. Further, the apertures 160 in the base layer 132 may be in fluid communication with the interface manifold 120 and tissue surrounding the tissue site 104.

The apertures 160 in the base layer 132 may have any shape, such as, for example, circles, squares, stars, ovals, polygons, slits, complex curves, rectilinear shapes, triangles, or other shapes. The apertures 160 may be formed by cutting, by application of local RF energy, or other suitable techniques for forming an opening. Each of the apertures 160 of the plurality of apertures 160 may be substantially circular in shape, having a diameter and an area. The area of the apertures 160 described in the illustrative embodiments herein may be substantially similar to the area in other embodiments for the apertures 160 that may have non-circular shapes. Further, the area of each of the apertures 160 may be substantially the same, or each of the areas may vary, for example, based on the position of the aperture 160 in the base layer 132. For example, the area of the apertures 160 in the periphery 152 of the base layer 132 may be larger than the area of the apertures 160 in the central portion 156 of the base layer 132. The apertures 160 may have a uniform pattern or may be randomly distributed on the base layer 132. The size and configuration of the apertures 160 may be designed to control the adherence of the dressing 124 to the epidermis 106 as described herein.

In some embodiments, the apertures 160 positioned in the periphery 152 may be apertures 160a, the apertures 160 positioned at the corners 158 of the periphery 152 may be apertures 160b, and the apertures 160 positioned in the central portion 156 may be apertures 160c. In some embodiments, the apertures 160a may have an area greater than the apertures 160b. Further, in some embodiments, the apertures 160b may have an area greater than the apertures 160c. The dimensions of the base layer 132 may be increased or decreased, for example, substantially in proportion to one another to suit a particular application or usage. Further, although the central portion 156, the border 161, and the periphery 152 of the base layer 132 are shown as having a substantially square shape, these and other components of the base layer 132 may have any shape to suit a particular application or usage.

In some embodiments, the base layer 132 may be a soft, pliable material suitable for providing a fluid seal with the tissue site 104 as described herein. For example, the base layer 132 may comprise, without limitation, a silicone gel; a soft silicone; hydrocolloid; hydrogel; polyurethane gel; polyolefin gel; hydrogenated styrenic copolymer gel; a foamed gel; a soft, closed-cell foam, such as polyurethanes and polyolefins coated with an adhesive; polyurethane; polyolefin; or hydrogenated styrenic copolymers. Further, in some embodiments, the base layer 132 may have a thickness between about 500 microns ($\mu$m) and about 1000 microns ($\mu$m). In some embodiments, the base layer 132 may have a hardness, stiffness, or durometer between about 5 Shore OO and about 80 Shore OO. Further, in some embodiments, the base layer 132 may be comprised of hydrophobic or hydrophilic materials.

In some embodiments (not shown), the base layer 132 may be a hydrophobic-coated material. For example, the base layer 132 may be formed by coating a spaced material, such as, for example, woven, nonwoven, molded, or extruded mesh with a hydrophobic material. The hydrophobic material for the coating may be a soft silicone, for example. In this manner, the adhesive 136 may extend through openings in the spaced material analogous to the apertures 160 as described herein.

In some embodiments, the adhesive 136 may be exposed to the apertures 160 in at least the periphery 152 of the base layer 132. Further, in some embodiments, the adhesive 136 may be positioned adjacent to, or positioned in fluid communication with, the apertures 160 in at least the periphery 152 of the base layer 132. Further, in some embodiments, the adhesive 136 may be exposed to or in fluid communication with tissue surrounding the tissue site 104 through the apertures 160 in the base layer 132. As described further herein and shown in FIG. 3, the adhesive 136 may extend, deform, or be pressed through the plurality of apertures 160 to contact the epidermis 106 for securing the dressing 124 to, for example, tissue surrounding the tissue site 104. The apertures 160 may provide sufficient contact of the adhesive 136 to the epidermis 106 to secure the dressing 124 about the tissue site 104. However, the configuration of the apertures 160 and the adhesive 136 may permit release and repositioning of the dressing 124 about the tissue site 104.

In some embodiments, the apertures 160b at the corners 158 of the periphery 152 may be smaller than the apertures 160a in other portions of the periphery 152. For a given geometry of the corners 158, the smaller size of the apertures 160b compared to the apertures 160a may enhance or increase the surface area of the adhesive 136 exposed to the apertures 160b and to tissue through the apertures 160b at the corners 158. The size and number of the apertures 160b in the corners 158 may be adjusted as necessary, depending on the chosen geometry of the corners 158, to enhance or increase the exposed surface area of the adhesive 136.

Similar to the apertures 160b in the corners 158, any of the apertures 160 may be adjusted in size and number to increase the surface area of the adhesive 136 exposed to or in fluid communication with the apertures 160 for a particular application or geometry of the base layer 132. For example, in some embodiments (not shown) the apertures 160b, or apertures of another size, may be positioned in the periphery 152 and at the border 161. Similarly, the apertures 160*b*, or apertures of another size, may be positioned as described above in other locations of the base layer 132 that may have a complex geometry or shape.

The adhesive 136 may be a medically-acceptable adhesive. In some embodiments, the adhesive 136 may be deformable or flowable. For example, the adhesive 136 may comprise, without limitation, an acrylic adhesive, rubber adhesive, high-tack silicone adhesive, polyurethane, or other adhesive substance. In some embodiments, the adhesive 136 may be a pressure-sensitive adhesive comprising an acrylic adhesive. In some embodiments, the adhesive 136 may be configured as a layer having substantially the same shape as the periphery 152 of the base layer 132. In some embodiments, the adhesive 136 may be continuous or discontinuous. Discontinuities in the adhesive 136 may be provided by apertures (not shown) in the adhesive 136. Apertures in the adhesive 136 may be formed after application of the adhesive 136 or by coating the adhesive 136 in patterns on a carrier layer, such as, for example, a side of the sealing member 140 adapted to face the epidermis 106. Further, discontinuities or apertures in the adhesive 136 may be sized to control the amount of the adhesive 136 extending through the apertures 160 in the base layer 132 to reach the epidermis 106. Discontinuities or apertures in the adhesive 136 may also be sized to enhance the Moisture Vapor Transfer Rate (MVTR) of the dressing 124 as described herein.

Factors that may be utilized to control the adhesion strength of the dressing 124 may include the diameter, area, and number of the apertures 160 in the base layer 132; the thickness of the base layer 132; the thickness and amount of the adhesive 136; and the tackiness of the adhesive 136. An increase in the amount of the adhesive 136 extending through the apertures 160 may correspond to an increase in the adhesion strength of the dressing 124. A decrease in the thickness of the base layer 132 may correspond to an increase in the amount of adhesive 136 extending through the apertures 160. Thus, the diameter, area, and configuration of the apertures 160; the thickness of the base layer 132; and the amount and tackiness of the adhesive utilized may be varied to provide a desired adhesion strength for the dressing 124.

In some embodiments, the tackiness of the adhesive 136 may vary in different locations of the base layer 132. For example, in locations of the base layer 132 where the apertures 160 are comparatively large, such as the apertures 160*a*, the adhesive 136 may have a lower tackiness than other locations of the base layer 132 where the apertures 160 are smaller, such as the apertures 160*b* and 160*c*. In this manner, locations of the base layer 132 having larger apertures 160 and lower tackiness adhesive 136 may have an adhesion strength comparable to locations having smaller apertures 160 and higher tackiness adhesive 136.

A release liner 162 may be attached to or positioned adjacent to the base layer 132 to protect the adhesive 136 prior to application of the dressing 124 to the tissue site 104. Prior to application of the dressing 124 to the tissue site 104, the base layer 132 may be positioned between the sealing member 140 and the release liner 162. Removal of the release liner 162 may expose the base layer 132 and the adhesive 136 for application of the dressing 124 to the tissue site 104. The release liner 162 may also provide stiffness to assist with, for example, deployment of the dressing 124. The release liner 162 may be, for example, a casting paper, a film, or polyethylene. Further, the release liner 162 may be a polyester material such as polyethylene terephthalate (PET), or similar polar semi-crystalline polymer. The use of a polar semi-crystalline polymer for the release liner 162 may substantially preclude wrinkling or other deformation of the dressing 124. For example, the polar semi-crystalline polymer may be highly orientated and resistant to softening, swelling, or other deformation that may occur when brought into contact with components of the dressing 124, or when subjected to temperature or environmental variations, or sterilization. Further, a release agent may be disposed on a side of the release liner 162 configured to contact the base layer 132. For example, the release agent may be a silicone coating, and may have a release factor suitable to facilitate removal of the release liner 162 by hand and without damaging or deforming the dressing 124. In some embodiments, the release agent may be fluorosilicone. In other embodiments, the release liner 162 may be uncoated or otherwise used without a release agent.

Continuing with FIGS. 1-4B, the sealing member 140 may also be referred to as a dressing sealing member 140. The sealing member 140 may have a periphery 164 and a central portion 168. The sealing member 140 may additionally include a sealing member aperture such as an aperture 170. The periphery 164 of the sealing member 140 may be positioned proximate to the periphery 152 of the base layer 132 such that the central portion 168 of the sealing member 140 and the central portion 156 of the base layer 132 define an enclosure 172. The adhesive 136 may be positioned at least between the periphery 164 of the sealing member 140 and the periphery 152 of the base layer 132. The sealing member 140 may cover the tissue site 104 and the interface manifold 120 to provide a fluid seal and a sealed space 174 between the tissue site 104 and the sealing member 140 of the dressing 124. Herein, the fluid seal and the sealed space 174 may also refer a sealed or closed volume defined by the system 102, which may be required to maintain reduced pressure, to treat, or to protect the tissue site 104, for example. Further, the sealing member 140 may cover other tissue, such as a portion of the epidermis 106, surrounding the tissue site 104 to provide the fluid seal between the sealing member 140 and the tissue site 104. In some embodiments, a portion of the periphery 164 of the sealing member 140 may extend beyond the periphery 152 of the base layer 132 and into direct contact with tissue surrounding the tissue site 104. In other embodiments, the periphery 164 of the sealing member 140, for example, may be positioned in contact with tissue surrounding the tissue site 104 to provide the sealed space 174 without the base layer 132. Thus, the adhesive 136 may also be positioned at least between the periphery 164 of the sealing member 140 and tissue, such as the epidermis 106, surrounding the tissue site 104. The adhesive 136 may be disposed on a surface of the sealing member 140 adapted to face the tissue site 104 and the base layer 132.

The sealing member 140 may be formed from any material that allows for a fluid seal. A fluid seal may be a seal adequate to maintain reduced pressure at a desired site given the particular reduced pressure source or system involved. The sealing member 140 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber;

ethylene propylene diene monomer; chlorosulfonated polyethylene; polysulfide rubber; polyurethane (PU); EVA film; co-polyester; silicones; a silicone drape; a 3M TEGADERM® drape; a polyurethane (PU) drape, such as one available from Avery Dennison Corporation of Pasadena, California; polyether block polyamide copolymer (PEBAX), for example, from Arkema, France; Expopack 2327; or other appropriate material.

The sealing member 140 may be vapor permeable and liquid impermeable, thereby allowing vapor and inhibiting liquids from exiting the sealed space 174 provided by the dressing 124. In some embodiments, the sealing member 140 may be a flexible, breathable film, membrane, or sheet having a high MVTR of, for example, at least about 300 g/m$^2$ per 24 hours. In other embodiments, a low or no vapor transfer drape may be used. The sealing member 140 may comprise a range of medically suitable films having a thickness between about 15 microns (μm) to about 50 microns (μm).

The fluid management assembly 144 may be disposed in the enclosure 172. In some embodiments, the fluid management assembly 144 may include a first dressing wicking layer 176, a second dressing wicking layer 180, and an absorbent layer 184. The absorbent layer 184 may be configured as a layer in some embodiments. However, the absorbent layer 184 is not limited to such a layered configuration or any particular shape. Thus, the absorbent layer 184 may be referred to interchangeably as a dressing absorbent 184 or an absorbent 184. The absorbent layer 184 may be positioned in fluid communication between the first dressing wicking layer 176 and the second dressing wicking layer 180. The first dressing wicking layer 176 may have a grain structure adapted to wick fluid along a surface of the first dressing wicking layer 176. Similarly, the second dressing wicking layer 180 may have a grain structure adapted to wick fluid along a surface of the second dressing wicking layer 180. For example, the first dressing wicking layer 176 and the second dressing wicking layer 180 may wick or otherwise transport fluid in a lateral direction along the surfaces of the first dressing wicking layer 176 and the second dressing wicking layer 180, respectively. The surface of the first dressing wicking layer 176 may be normal relative to the thickness of the first dressing wicking layer 176, and the surface of the second dressing wicking layer 180 may be normal relative to the thickness of the second dressing wicking layer 180. The wicking of fluid along the first dressing wicking layer 176 and the second dressing wicking layer 180 may enhance the distribution of the fluid over a surface area of the absorbent layer 184, which may increase absorbent efficiency and resist fluid blockages. Fluid blockages may be caused by, for example, fluid pooling at a particular location on or in the absorbent layer 184 rather than being distributed more uniformly across the absorbent layer 184. The laminate combination described for the first dressing wicking layer 176, the second dressing wicking layer 180, and the absorbent layer 184 may be adapted to maintain an open structure, resistant to blockage, capable of maintaining fluid communication with, for example, the tissue site 104.

In some embodiments, a peripheral portion 186 of the first dressing wicking layer 176 may be coupled to a peripheral portion 187 of the second dressing wicking layer 180 to define a wicking layer enclosure 188 between the first dressing wicking layer 176 and the second dressing wicking layer 180. Further, in some embodiments, the wicking layer enclosure 188 may surround or otherwise encapsulate the absorbent layer 184 between the first dressing wicking layer 176 and the second dressing wicking layer 180. The configuration of the first dressing wicking layer 176 and the second dressing wicking layer 180 in the fluid management assembly 144 may preference fluid away from the tissue site 104 and prevent the fluid from returning to the tissue site 104 prior to removal of the fluid from the dressing 124, for example, by the application of reduced pressure. The wicking layer enclosure 188 may enhance this ability to preference fluid away from the tissue site 104 and to prevent the fluid from returning to the tissue site 104.

Figure 5:
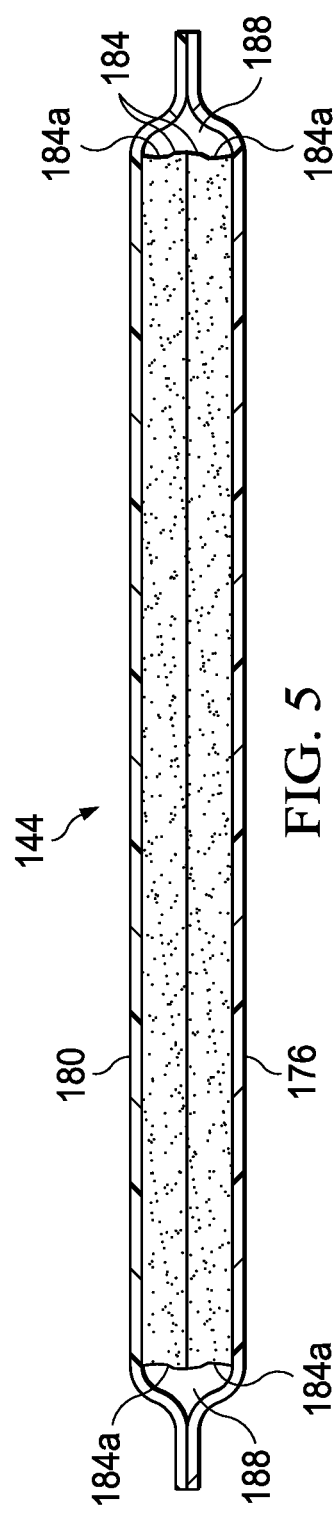
FIG. 5 is a cut-away view of an illustrative example of a fluid management assembly suitable for use with the dressing and system of FIG. 1.
Figure 6:
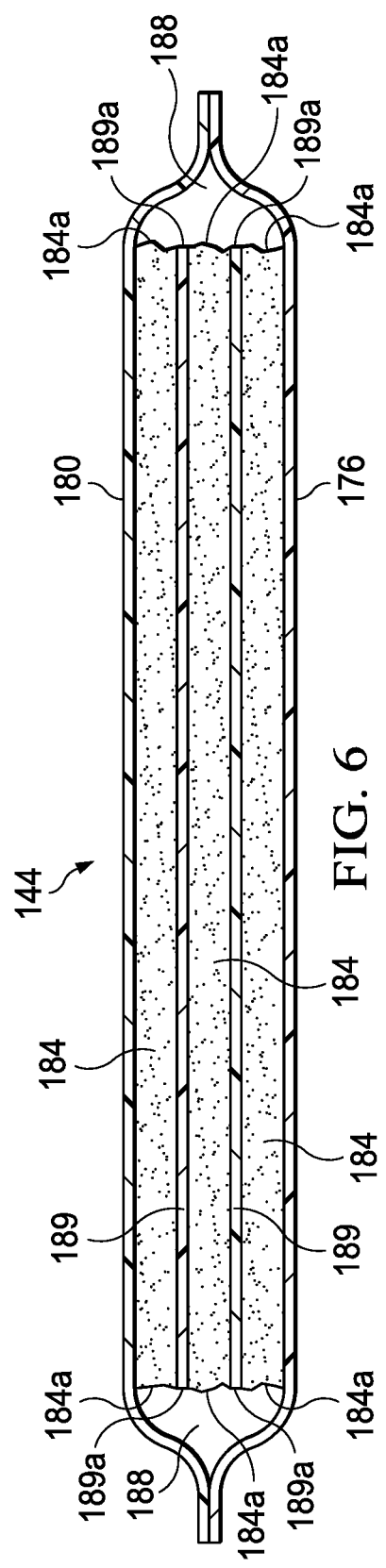
FIG. 6 is a cut-away view of another illustrative example of a fluid management assembly suitable for use with the dressing and system of FIG. 1.

Referring to FIGS. 5 and 6, in some embodiments, the fluid management assembly 144 may include, without limitation, any number of wicking layers and absorbent layers as desired for treating a particular tissue site. For example, the absorbent layer 184 may be a plurality of absorbent layers 184 positioned in fluid communication between the first dressing wicking layer 176 and the second dressing wicking layer 180. Further, as shown in FIG. 6, in some embodiments, at least one intermediate wicking layer 189 may be disposed in fluid communication between the plurality of absorbent layers 184. Similar to the absorbent layer 184, the plurality of absorbent layers 184 and the at least one intermediate wicking layer 189 may be positioned within the wicking layer enclosure 188. In some embodiments, the absorbent layer 184 may be disposed between the sealing member 140 and the interface manifold 120, and the first dressing wicking layer 176 and the second dressing wicking layer 180 may be omitted.

Continuing with FIGS. 5 and 6, sides 184a of the absorbent layers 184 may remain in fluid communication with one another for enhancing efficiency. Similarly, sides 189a of the at least one intermediate wicking layer 189 shown in FIG. 6 may remain in fluid communication with one another and with the sides 184a of the absorbent layers 184. Further, including additional absorbent layers 184 may increase the absorbent mass of the fluid management assembly 144 and generally provide greater fluid capacity. However, for a given absorbent mass, multiple light coat-weight absorbent layers 184 may be utilized rather than a single heavy coat-weight absorbent layer 184 to provide a greater absorbent surface area for further enhancing the absorbent efficiency.

In some embodiments, the absorbent layer 184 may be a hydrophilic material adapted to absorb fluid from, for example, the tissue site 104. Materials suitable for the absorbent layer 184 may include, without limitation, super absorbent polymers and similar absorbent materials; LUQUAFLEECE® material; TEXSUS FP2326; BASF 402C; Technical Absorbents 2317, available from Technical Absorbents, Ltd. of Lincolnshire, United Kingdom; sodium polyacrylate super absorbers; cellulosics (carboxy methyl cellulose and salts such as sodium CMC); or alginates. Materials suitable for the first dressing wicking layer 176 and the second dressing wicking layer 180 may include, without limitation, any material having a grain structure capable of wicking fluid as described herein, such as, for example, LIBELTEX TDL2, 80 gsm, or similar materials, which may be non-woven.

The fluid management assembly 144 may be manufactured as a pre-laminated structure, or supplied as individual layers of material that can be stacked or layered upon one another as described herein. Individual layers of the fluid management assembly 144 may be bonded or otherwise secured to one another without adversely affecting fluid management by, for example, utilizing a solvent or non-solvent adhesive, or by thermal welding. Further, the fluid management assembly 144 may be coupled to the border 161 of the base layer 132 in any suitable manner, such as, for example, by a weld or an adhesive. The border 161, being free of the apertures 160 as described for some embodiments, may provide a flexible barrier between the fluid management assembly 144 and the tissue site 104 for enhancing comfort.

The dressing 124 may be modified in various embodiments to suit a particular application or usage. For example, in some embodiments, the first dressing wicking layer 176 or the second dressing wicking layer 180 may be omitted along with the absorbent layer 184 and the base layer 132. In such an embodiment, the dressing 124 may comprise the sealing member 140 and one of the first dressing wicking layer 176 or the second dressing wicking layer 180 for disposing in the sealed space 174 between the sealing member 140 and the tissue site 104. Further, in some embodiments, the fluid management assembly 144 may be omitted from the dressing 124, and a dressing manifold (not shown) may be positioned in the enclosure 172 in place of the fluid management assembly 144. The dressing manifold may be configured as a layer and may be comprised of any material suitable for removing fluids from a tissue site through a plurality of pores, pathways, or flow channels as described herein, such as, without limitation, a foam, a woven material, a cast silicone, a polyurethane material, or any of the materials recited above for the interface manifold 120. Further, in some embodiments, the dressing 124 may be modified by omitting the base layer 132 and replacing the fluid management assembly 144 with the above-described dressing manifold. In such an embodiment, the dressing 124 may comprise the sealing member 140 and the dressing manifold for disposing in the sealed space 174 between the sealing member 140 and the tissue site 104. Further, in some embodiments, the absorbent layer 184 may be omitted and replaced with the dressing manifold such that the dressing manifold is positioned between the first dressing wicking layer 176 and the second dressing wicking layer 180.

Referring back to FIGS. 1 and 2, in some embodiments, the enclosure 172 between the base layer 132 and the sealing member 140 may include an optional anti-microbial layer 190. In some embodiments, the anti-microbial layer 190 may be positioned in the sealed space 174. The addition of the anti-microbial layer 190 may reduce the probability of excessive bacterial growth within the dressing 124 to permit the dressing 124 to remain in place for an extended period. The anti-microbial layer 190 may be, for example, an additional layer included as a part of the fluid management assembly 144, or a coating of an anti-microbial agent disposed in any suitable location within the dressing 124. The anti-microbial layer 190 may be comprised of elemental silver or a similar compound, for example. In some embodiments, the anti-microbial agent may be formulated in any suitable manner and associated with other components of the dressing 124.

Continuing with FIGS. 1 and 2, the conduit interface 148 may be positioned proximate to or coupled to the sealing member 140 and in fluid communication with the enclosure 172 of the dressing 124. For example, the conduit interface 148 may be in fluid communication with the dressing 124 through the aperture 170 in the sealing member 140. The conduit interface 148 may provide reduced pressure from the reduced-pressure source 128 to the dressing 124. The conduit interface 148 may also be adapted to be positioned in fluid communication with the optional interface manifold 120. An optional liquid trap 192 may be positioned in fluid communication between the dressing 124 and the reduced-pressure source 128. The liquid trap 192 may be any suitable containment device having a sealed internal volume capable of retaining liquid, such as condensate or other liquids.

The conduit interface 148 may comprise a medical-grade, soft polymer or other pliable material. As non-limiting examples, the conduit interface 148 may be formed from polyurethane, polyethylene, polyvinyl chloride (PVC), fluorosilicone, or ethylene-propylene. In some illustrative, non-limiting embodiments, conduit interface 148 may be molded from DEHP-free PVC. The conduit interface 148 may be formed in any suitable manner such as by molding, casting, machining, or extruding. Further, the conduit interface 148 may be formed as an integral unit or as individual components and may be coupled to the dressing 124 by, for example, adhesive or welding.

In some embodiments, the conduit interface 148 may be formed of an absorbent material having absorbent and evaporative properties. The absorbent material may be vapor permeable and liquid impermeable, thereby being configured to permit vapor to be absorbed into and evaporated from the material through permeation while inhibiting permeation of liquids. The absorbent material may be, for example, a hydrophilic polymer such as a hydrophilic polyurethane. Although the term hydrophilic polymer may be used in the illustrative embodiments that follow, any absorbent material having the properties described herein may be suitable for use in the system 102. Further, the absorbent material or hydrophilic polymer may be suitable for use in various components of the system 102 as described herein.

The use of such a hydrophilic polymer for the conduit interface 148 may permit liquids in the conduit interface 148 to evaporate, or otherwise dissipate, during operation. For example, the hydrophilic polymer may allow the liquid to permeate or pass through the conduit interface 148 as vapor, in a gaseous phase, and evaporate into the atmosphere external to the conduit interface 148. Such liquids may be, for example, condensate or other liquids. Condensate may form, for example, as a result of a decrease in temperature within the conduit interface 148, or other components of the system 102, relative to the temperature at the tissue site 104. Removal or dissipation of liquids from the conduit interface 148 may increase visual appeal and prevent odor. Further, such removal of liquids may also increase efficiency and reliability by reducing blockages and other interference with the components of the system 102.

Similar to the conduit interface 148, the liquid trap 192, and other components of the system 102, may also be formed of an absorbent material or a hydrophilic polymer. The absorptive and evaporative properties of the hydrophilic polymer may also facilitate removal and dissipation of liquids residing in the liquid trap 192, and other components of the system 102, by evaporation. Such evaporation may leave behind a substantially solid or gel-like waste. The substantially solid or gel-like waste may be cheaper to dispose than liquids, providing a cost savings for operation of the system 102. The hydrophilic polymer may be used for other components in the system 102 where the management of liquids is beneficial.

In some embodiments, the absorbent material or hydrophilic polymer may have an absorbent capacity in a saturated state that is substantially equivalent to the mass of the hydrophilic polymer in an unsaturated state. The hydrophilic polymer may be fully saturated with vapor in the saturated state and substantially free of vapor in the unsaturated state. In both the saturated state and the unsaturated state, the hydrophilic polymer may retain substantially the same physical, mechanical, and structural properties. For example, the hydrophilic polymer may have a hardness in the unsaturated state that is substantially the same as a hardness of the hydrophilic polymer in the saturated state. The hydrophilic polymer and the components of the system 102 incorporating the hydrophilic polymer may also have a size that is substantially the same in both the unsaturated state and the saturated state. Further, the hydrophilic polymer may remain dry, cool to the touch, and pneumatically sealed in the saturated state and the unsaturated state. The hydrophilic polymer may also remain substantially the same color in the saturated state and the unsaturated state. In this manner, this hydrophilic polymer may retain sufficient strength and other physical properties to remain suitable for use in the system 102. An example of such a hydrophilic polymer is offered under the trade name Techophilic HP-93A-100, available from The Lubrizol Corporation of Wickliffe, Ohio, United States. Techophilic HP-93A-100 is an absorbent hydrophilic thermoplastic polyurethane capable of absorbing 100% of the unsaturated mass of the polyurethane in water and having a durometer or Shore Hardness of about 83 Shore A.

Continuing with FIGS. 1 and 2, the reduced-pressure source 128 may provide reduced pressure to the dressing 124 and the sealed space 174. The reduced-pressure source 128 may be any suitable device for providing reduced pressure, such as, for example, a vacuum pump; a wall suction system, such as those common to hospitals and clinics; a hand pump; a manual pump; a powered pump, such as an electronic pump, or similar source. In some embodiments, the reduced-pressure source 128 may be a component of the therapy unit 130. The therapy unit 130 may include control circuitry and sensors, such as, without limitation, a pressure sensor (not shown) or a moisture sensor (not shown). The pressure sensor may be configured to sense reduced pressure in the dressing 124 or at the tissue site 104. The moisture sensor may be configured to sense moisture level in the dressing 124 or at the tissue site 104. Reduced pressure or moisture levels in the dressing 124 or the tissue site 104 may be controlled or monitored based on a signal generated by the pressure sensor or the moisture sensor. For example, the therapy unit 130 may be configured to control the amount of reduced pressure from the reduced-pressure source 128 being applied to the tissue site 104 according to a user input and a reduced-pressure feedback signal generated by the pressure sensor. Further, an alarm or other output device may be controlled by a moisture level signal or a saturation level signal generated by the moisture sensor and corresponding to a moisture level or a saturation level in the dressing 124. Such an alarm or other output device may be used to inform a caretaker or user that the dressing 124 is fully saturated or requires replacement. For example, the alarm or output device may be a visual or audible indicator, or a component configured to shut-down the system 102 or discontinue treatment, such as a valve configured to vent the system 102 or the dressing 124 to atmosphere.

As used herein, "reduced pressure" may refer to a pressure less than the ambient pressure at a tissue site being subjected to treatment. In some embodiments, the reduced pressure may be less than the atmospheric pressure. Further, in some embodiments, the reduced pressure may also be less than a hydrostatic pressure at a tissue site. Unless otherwise indicated, values of pressure stated herein are gauge pressures. While the amount and nature of reduced pressure applied to a tissue site may vary according to the application, in some embodiments, the reduced pressure may be between −5 mm Hg and −500 mm Hg. In some embodiments, the reduced pressure may be between −100 mm Hg and −200 mm Hg.

The reduced pressure delivered may be, for example, constant, varied, patterned, or random. Further, the reduced pressure may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, an increase in reduced pressure or vacuum pressure may refer to a relative reduction in absolute pressure. Further, an increase in reduced pressure may correspond to a reduction in pressure (more negative relative to ambient pressure), and a decrease in reduced pressure may correspond to an increase in pressure (less negative relative to ambient pressure).

Continuing with FIGS. 1 and 2, a conduit 196 having an internal lumen 197 may be coupled in fluid communication between the reduced-pressure source 128 and the dressing 124. The internal lumen 197 may have an internal diameter between, for example, about 0.5 millimeters to about 3.0 millimeters. In some embodiments, the internal diameter of the internal lumen 197 may be between about 1 millimeter to about 2 millimeters. The conduit interface 148 may be coupled in fluid communication with the dressing 124 and adapted to connect between the conduit 196 and the dressing 124 for providing fluid communication with the reduced-pressure source 128. The conduit interface 148 may be fluidly coupled to the conduit 196 in any suitable manner, such as, for example, by an adhesive, solvent or non-solvent bonding, welding, or interference fit. The aperture 170 in the sealing member 140 may provide fluid communication between the dressing 124 and the conduit interface 148. For example, the conduit interface 148 may be in fluid communication with the enclosure 172 or the sealed space 174 through the aperture 170 in the sealing member 140. In some embodiments, the conduit 196 may be inserted into the dressing 124 through the aperture 170 in the sealing member 140 to provide fluid communication with the reduced-pressure source 128 without use of the conduit interface 148. The reduced-pressure source 128 may also be directly coupled in fluid communication with the dressing 124 or the sealing member 140 without use of the conduit 196. In some embodiments, the conduit 196 may be, for example, a flexible polymer tube. A distal end of the conduit 196 may include a coupling 198 for attachment to the reduced-pressure source 128.

The conduit 196 may have a conduit filter 199, such as, for example, a hydrophobic filter. The conduit filter 199 may be disposed in the internal lumen 197 such that fluid communication between the reduced-pressure source 128 and the dressing 124 is provided through the conduit filter 199. The conduit filter 199 may be, for example, a porous, sintered polymer cylinder sized to fit the dimensions of the internal lumen 197 to substantially preclude liquid from bypassing the cylinder. The conduit filter 199 may also be treated with an absorbent material adapted to swell when brought into contact with liquid to block the flow of the liquid. The conduit filter 199 may be positioned at any location within the internal lumen 197. However, positioning the conduit filter 199 within the internal lumen 197 closer toward the reduced-pressure source 128, rather than the dressing 124, may allow a user to detect the presence of liquid in the internal lumen 197.

In some embodiments, the conduit 196 and the coupling 198 may be formed of an absorbent material or a hydrophilic polymer as described above for the conduit interface 148. In this manner, the conduit 196 and the coupling 198 may permit liquids in the conduit 196 and the coupling 198 to evaporate, or otherwise dissipate, as described above for the conduit interface 148. The conduit 196 and the coupling 198 may be, for example, molded from the hydrophilic polymer separately, as individual components, or together as an integral component. Further, a wall of the conduit 196 defining the internal lumen 197 may be extruded from the hydrophilic polymer. The conduit 196 may be less than about 1 meter in length, but may have any length to suit a particular application.

Figure 7:
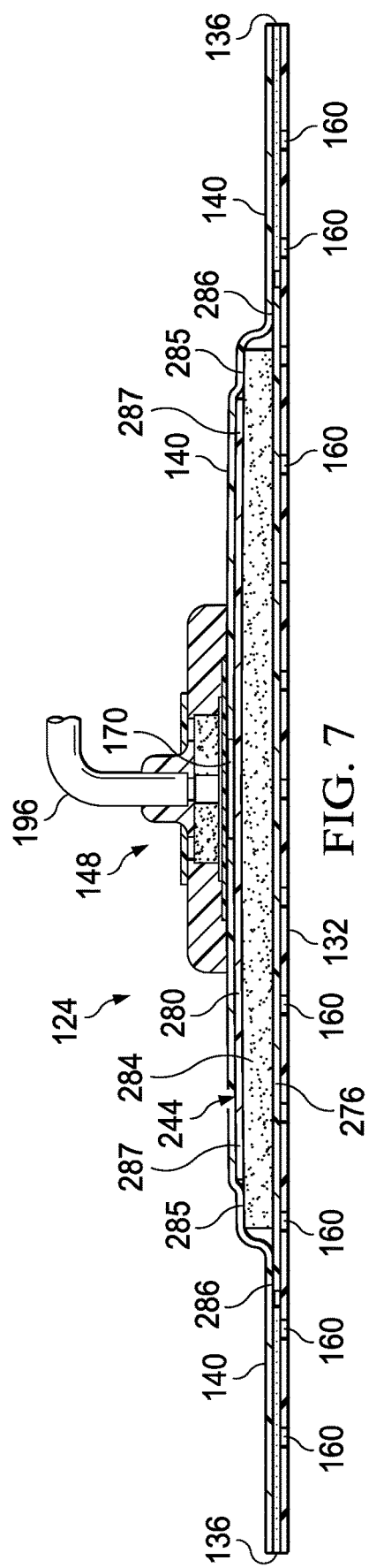
FIG. 7 is a cut-away view of another illustrative example of a dressing and a fluid management assembly suitable for use with the system of FIG. 1.

Referring to FIG. 7, another embodiment of a fluid management assembly 244 suitable for use with the dressing 124 and the system 102 is shown. The fluid management assembly 244 may include a first dressing wicking layer 276, a second dressing wicking layer 280, and an absorbent layer 284 comprised of substantially the same materials and properties as those described above in connection with the fluid management assembly 144. Thus, the first dressing wicking layer 276, the second dressing wicking layer 280, and the absorbent layer 284 may be analogous to the first dressing wicking layer 176, the second dressing wicking layer 180, and the absorbent layer 184, respectively.

In the fluid management assembly 244, the second dressing wicking layer 280 may have a peripheral portion 287. The second dressing wicking layer 280 and the peripheral portion 287 of the second dressing wicking layer 280 may be positioned in contact with the sealing member 140. The absorbent layer 284 may have a peripheral portion 285 extending beyond the peripheral portion 287 of the second dressing wicking layer 280. The absorbent layer 284 may be positioned adjacent to or proximate to the second dressing wicking layer 280 such that the peripheral portion 285 of the absorbent layer 284 is in contact with the sealing member 140 surrounding the peripheral portion 287 of the second dressing wicking layer 280. Similarly, the first dressing wicking layer 276 may have a peripheral portion 286 extending beyond the peripheral portion 285 of the absorbent layer 284. The first dressing wicking layer 276 may be positioned adjacent to or proximate to the absorbent layer 284 such that the peripheral portion 286 of the first dressing wicking layer 276 is in contact with the sealing member 140 surrounding the peripheral portion 285 of the absorbent layer 284. Further, the first dressing wicking layer 276 may be positioned adjacent to or proximate to the base layer 132. Thus, at least the peripheral portion 287, the peripheral portion 285, and the peripheral portion 286 may be coupled to the sealing member 140, such as, for example, by an adhesive coating disposed on a surface of the sealing member 140 facing the base layer 132. The adhesive coating may be analogous to the adhesive 136 that may be applied across the surface of the sealing member 140 facing the base layer 132. The second dressing wicking layer 280, the absorbent layer 284, and the first dressing wicking layer 276 may respectively have increasing surface areas to enhance contact with the adhesive coating described above. In other embodiments, the fluid management assembly 244 may include any number of absorbent layers and wicking layers for treating a particular tissue site.

Figure 8:
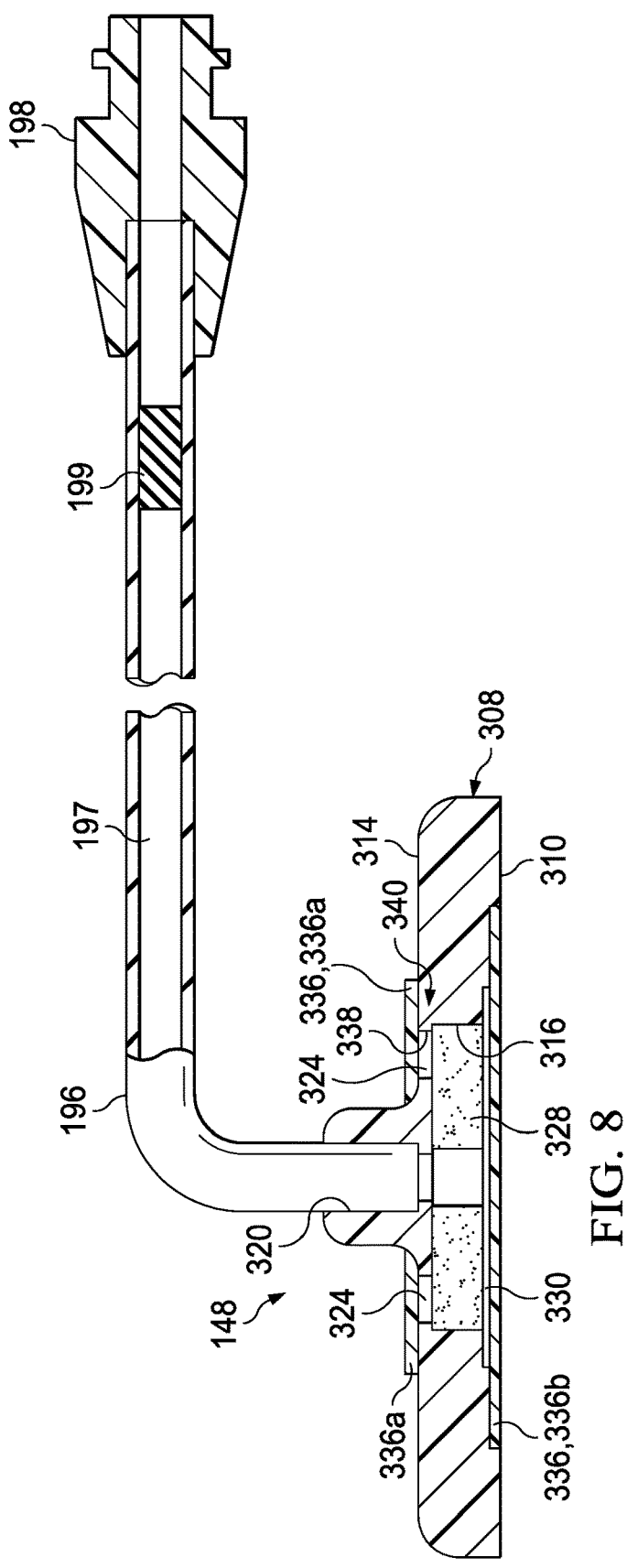
FIG. 8 is a cut-away view of an illustrative example of a conduit interface suitable for use with the dressing and system of FIG. 1.
Figure 10:
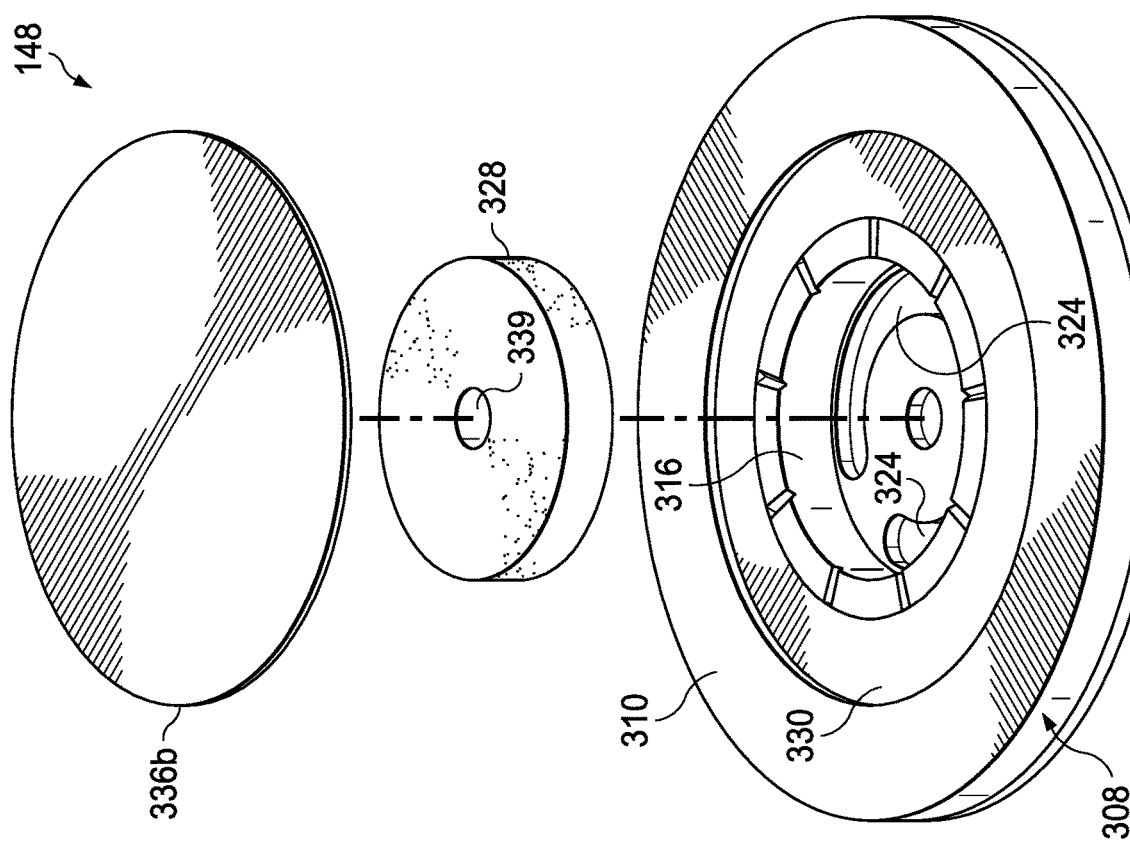
FIG. 10 is an exploded, perspective view from a bottom side of the conduit interface of FIG. 8.
Figure 9:
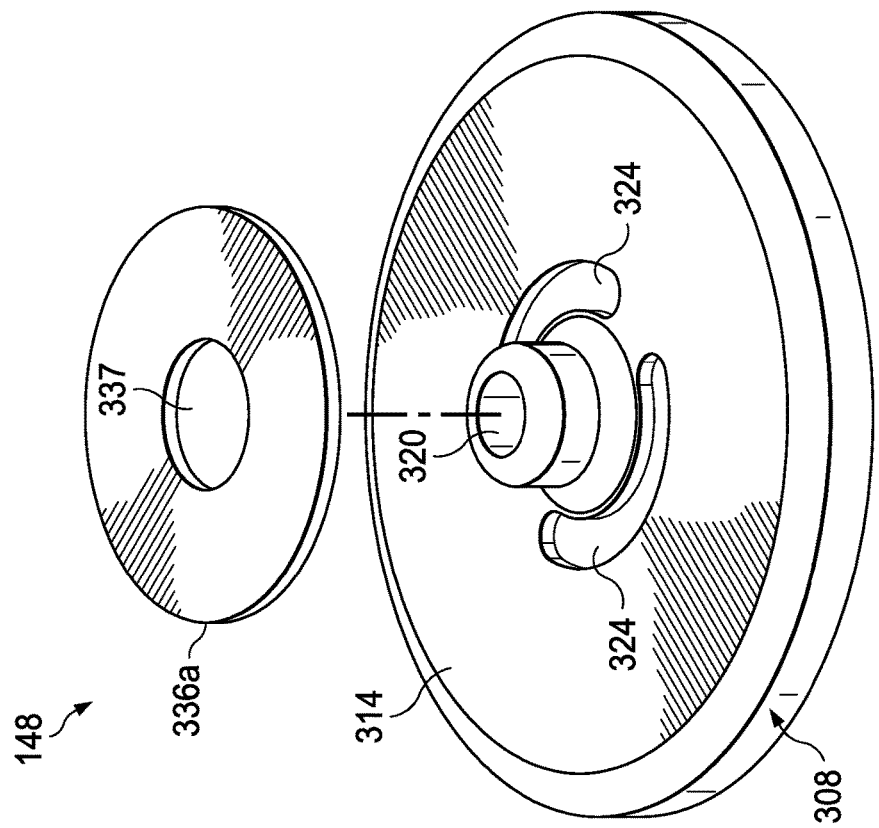
FIG. 9 is an exploded, perspective view from a top side of the conduit interface of FIG. 8.

Referring to FIGS. 8-10, in some embodiments, the conduit interface 148 may include a housing 308, a mounting surface 310, and an exterior-facing surface 314 positioned across from or opposite to the mounting surface 310. The mounting surface 310 and the exterior-facing surface 314 may be carried or defined by the housing 308 of the conduit interface 148. Further, in some embodiments, the conduit interface 148, or the housing 308 of the conduit interface 148, may include or carry an internal cavity 316, an inlet port 320, a vent 324, and a temporary plug 328.

The internal cavity 316 may have a cavity opening or an opening 330 that may be positioned proximate to, positioned on, or positioned at the mounting surface 310 such that the opening 330 may provide fluid communication from the mounting surface 310 to the internal cavity 316. The inlet port 320 may be in fluid communication with the internal cavity 316 through the exterior-facing surface 314. Thus, the inlet port 320 may permit fluid communication between or through the exterior-facing surface 314 and the mounting surface 310. The vent 324 may be in fluid communication with the internal cavity 316 through the exterior-facing surface 314. However, the temporary plug 328 may be configured to temporarily preclude fluid communication through the vent 324. In some embodiments, the temporary plug 328 may be enclosed by at least one conduit interface filter or hydrophobic filter 336. The at least one hydrophobic filter 336 may be vapor permeable and liquid impermeable such that vapor may pass through or permeate the hydrophobic filter 336 while precluding or blocking the passage of liquid. Herein, the temporary plug 328 may also be referred to as a transformable plug 328, and the inlet port 320 may also be referred to as a conduit connection port 320.

The conduit interface 148 may be configured to fluidly communicate with the dressing 124 for treating the tissue site 104. For example, the mounting surface 310 may be configured to be coupled to the dressing 124 such that the internal cavity 316 may be positioned in fluid communication with the dressing 124 through the opening 330. Thus, the inlet port 320 may be configured to provide or to be in fluid communication with the dressing 124, or the sealed space 174 that may be provided by the dressing 124 at the tissue site 104. Further, the inlet port 320 may be configured to communicate reduced pressure from the reduced pressure source 128 to the internal cavity 316 and to the sealed space 174. The internal cavity 316 may be housed between the mounting surface 310 and the exterior-facing surface 314. The inlet port 320 and the vent 324 may be positioned on, positioned at, or positioned proximate to the exterior-facing surface 314. The vent 324 may be configured to be in fluid communication between the sealed space 174 and an atmosphere exterior to the sealed space 174 when not occluded by the temporary plug 328, in some embodiments. Further, when not occluded by the temporary plug 328, the vent 324 may be in fluid communication with the inlet port 320 such that the inlet port 320 may be in fluid communication with atmosphere or ambient air exterior to the exterior-facing surface 314 through the vent 324.

In some embodiments, the temporary plug 328 may be positioned in fluid communication between the inlet port 320 and the vent 324, or in fluid communication between the internal cavity 316 and the vent 324, such that the temporary plug 328 may temporarily preclude fluid communication through the vent 324 as described herein. Further, in some embodiments, the temporary plug 328 may be positioned in the vent 324, or in a fluid passageway 338 defined by the vent 324 between the internal cavity 316 and the exterior-facing surface 314. Even further, in some embodiments, the temporary plug 328 may be positioned proximate to the inlet port 320. Even further, in some embodiments (not shown), a temporary plug analogous to the temporary plug 328 and a vent analogous to the vent 324 may be positioned or associated with other components of the system 102 that may be capable of being opened to the atmosphere, such as, without limitation, the conduit 196 or the sealing member 140.

In some embodiments, the dressing 124 may include the inlet port 320 and a valve 340. In some embodiments, the inlet port 320 and the valve 340 may be carried by the conduit interface 148. However, in other embodiments, the inlet port 320 and the valve 340 may be associated with the dressing 124 or the system 102 in any suitable manner. For example, a valve analogous to the valve 340 may be positioned or associated with other components of the system 102 that may be capable of being opened to the atmosphere.

As described herein, the inlet port 320 may be configured to provide fluid communication to the dressing 124. The valve 340 may be configured to be activated from a closed position to an open position based on a liquid saturation level in the dressing 124. Further, the valve 340 may be configured to preclude fluid communication to ambient air external to the dressing 124 in the closed position and to permit fluid communication to the ambient air in the open position.

In some embodiments, the valve 340 may include the vent 324 and the temporary plug 328. As described herein, the vent 324 may be configured to provide fluid communication to ambient air, and the temporary plug 328 may be positioned to preclude fluid communication through the vent 324 when the valve 340 is in the closed position. In some embodiments, the temporary plug 328 may be fluid impermeable when the valve 340 is in the closed position and fluid permeable when the valve 340 is in the open position. The temporary plug 328 may be configured to deteriorate or dissolve when the valve 340 is activated from the closed position to the open position. In some embodiments, the valve 340 may be configured to be activated based on a fluid or liquid saturation level of the absorbent 184, which may be included in the dressing 124. In other embodiments (not shown), the valve 340 may be a mechanical valve, a solenoid valve, or any suitable type of valve that may be associated with the dressing 124 or conduit interface 148 in a manner consistent with this disclosure.

Referring to FIGS. 9-10, in some embodiments, the at least one hydrophobic filter 336 may be a first hydrophobic filter 336a and a second hydrophobic filter 336b. The first hydrophobic filter 336a may be positioned covering the vent 324 proximate to the exterior-facing surface 314. The second hydrophobic filter 336b may be positioned covering the opening 330 proximate to the mounting surface 310. The temporary plug 328 may be positioned between the first hydrophobic filter 336a and the second hydrophobic filter 336b. In some embodiments, the first hydrophobic filter 336a may be configured to be positioned in fluid communication between the atmosphere and the temporary plug 328, and the second hydrophobic filter 336b may be configured to be positioned in fluid communication between the temporary plug 328 and the sealed space 174. The atmosphere may be ambient air exterior to the sealed space 174.

In some embodiments, the vent 324 may be positioned proximate to the inlet port 320 and around the inlet port 320. For example, the vent 324 may have an annular or circular shape sized and positioned to substantially surround the inlet port 324. Further, more than one of the vent 324, or multiple sections of the vent 324, may be positioned around the inlet port 320 as shown in FIGS. 9-10 and described herein. Although FIGS. 9-10 depict the vent 324 in an annular or circular shape, the vent 324 may have any suitable shape capable of being positioned as described herein.

Further, in some embodiments, the first hydrophobic filter 336a may include a filter aperture 337 sized to be positioned about the inlet port 320 such that the first hydrophobic filter 336a may be positioned around or surrounding the inlet port 320. In other embodiments, the first hydrophobic filter 336a may have any suitable shape capable of being positioned as described herein. Further, in some embodiments, the temporary plug 328 may include a plug aperture 339 positioned in fluid communication with the inlet port 320. The plug aperture 339 may provide fluid communication between the inlet port 320 and the sealed space 174 through the temporary plug 328. Although FIGS. 9-10 depict the temporary plug 328 in an annular or circular shape, the temporary plug 328 may have any suitable shape capable of being positioned as described herein.

Figure 11A:
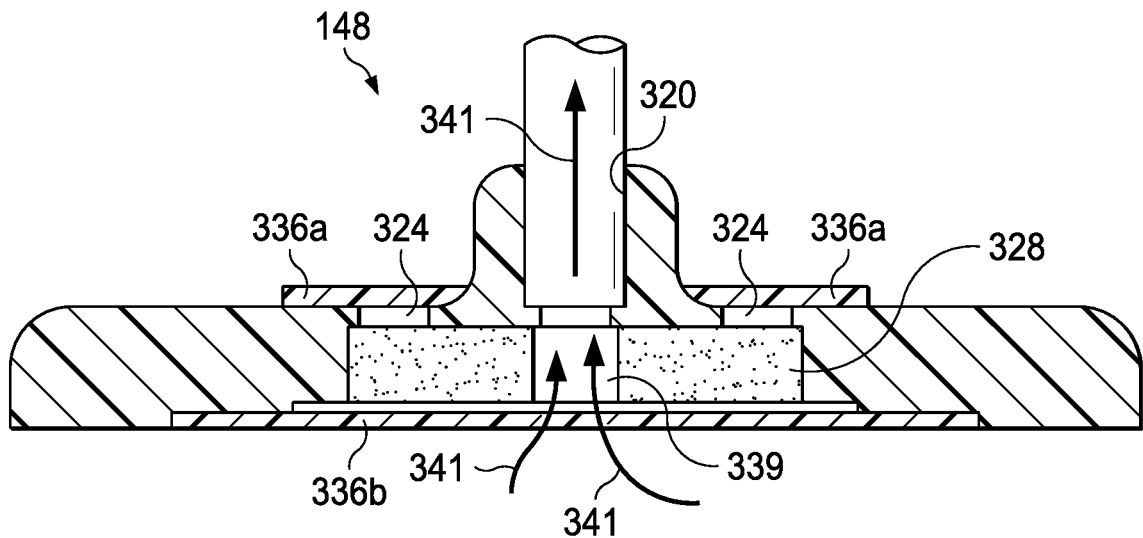
FIG. 11A depicts an illustrative example of fluid flow through the conduit interface of FIG. 8 with an illustrative example of a temporary plug in a serviceable state.
Figure 11B:
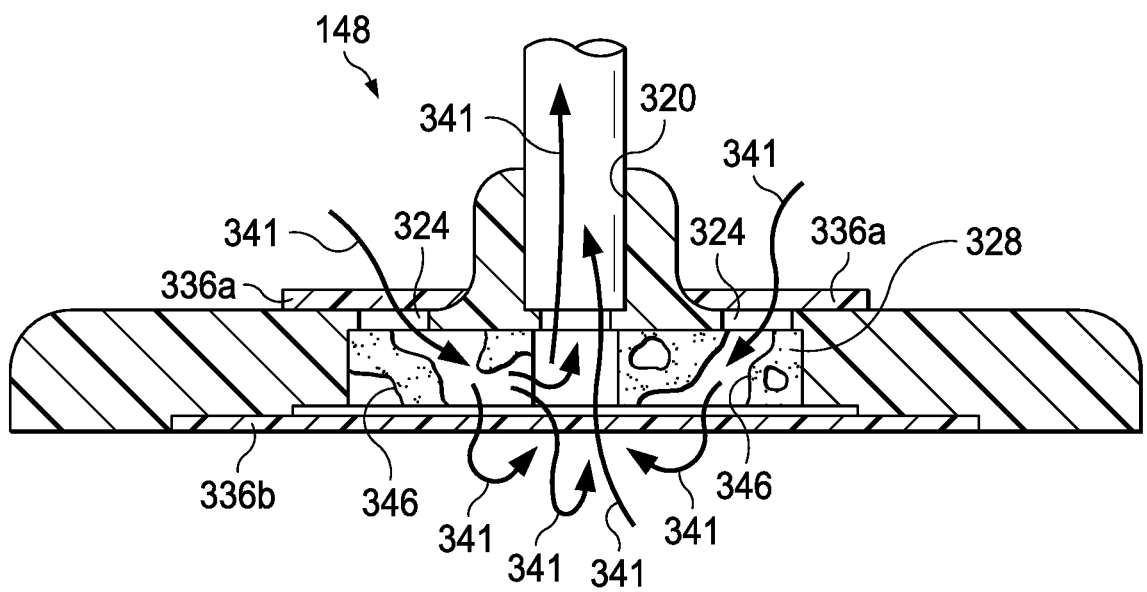
FIG. 11B depicts an illustrative example of fluid flow through the conduit interface of FIG. 8 with the temporary plug of FIG. 11A in a deteriorated state.

Referring to FIGS. 11A-11B, in some embodiments, the temporary plug 328 may be configured to change from a serviceable state, shown in FIG. 11A, to a deteriorated state, shown in FIG. 11B. The temporary plug 328 may be configured to seal or pneumatically seal the vent 324 when in the serviceable state and to open the vent 324 when in the deteriorated state. The temporary plug 328 may be configured to preclude fluid communication through the vent 324 in the serviceable state and to permit fluid communication through the vent 324 in the deteriorated state. For example, the temporary plug 328 may be fluid impermeable in the serviceable state and fluid permeable in the deteriorated state. When the temporary plug 328 is in the serviceable state shown in the illustrative example of FIG. 11A, fluid cannot flow through the vent 324. Accordingly, fluid flow arrows 341 in FIG. 11A illustrate fluid passing through the second hydrophobic filter 336b, the plug aperture 339, and the inlet port 320 without fluid passing through the vent 324. In contrast, fluid flow arrows 341 shown in FIG. 11B illustrate fluid passing through first hydrophobic filter 336a, the vent 324, and the temporary plug 328 in addition to fluid passing through the second hydrophobic filter 336b, the plug aperture 339, and the inlet port 320. Further, FIG. 11B illustrates ambient air being drawn through the vent 324, through the temporary plug 328 and other components of the conduit interface 148, and to the inlet port 320. When the temporary plug 328 is in the deteriorated state, fluid communication or passage may occur through the temporary plug 328 through at least one fluid channel 346 that may develop, open, or become defined in or through the temporary plug 328 when in the deteriorated state. In some embodiments, at least a portion of the fluid channels 346 may be defined by interconnected pores that may comprise a substrate material of the temporary plug 328 as described herein.

In some embodiments, the temporary plug 328 may be configured to change from the serviceable state to the deteriorated state after being exposed to moisture for a pre-determined time period. In some embodiments, the moisture may be a vapor that permeates the hydrophobic filter 336, such as, for example, the hydrophobic filter 336b, during operation.

Further, in some embodiments, the temporary plug 328 may be may be configured to change from the serviceable state to the deteriorated state in response to a liquid saturation level of the absorbent 184. The absorbent 184 may be included in the dressing 124 and configured to be positioned in the sealed space 174 and between the tissue site 104 and the sealing member 140.

Figure 12A:
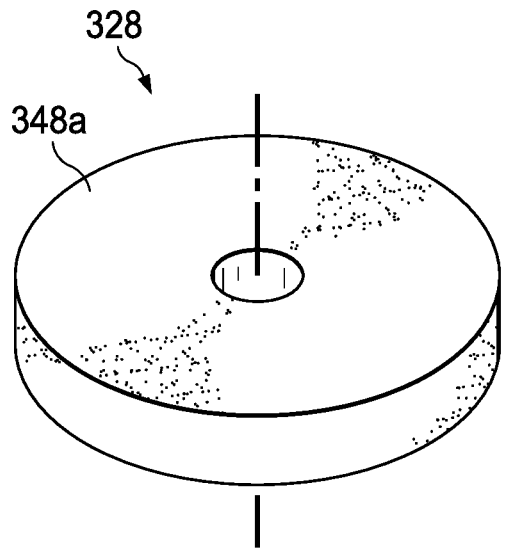
FIG. 12A is a perspective view of an illustrative example of a temporary plug in a serviceable state.
Figure 12B:
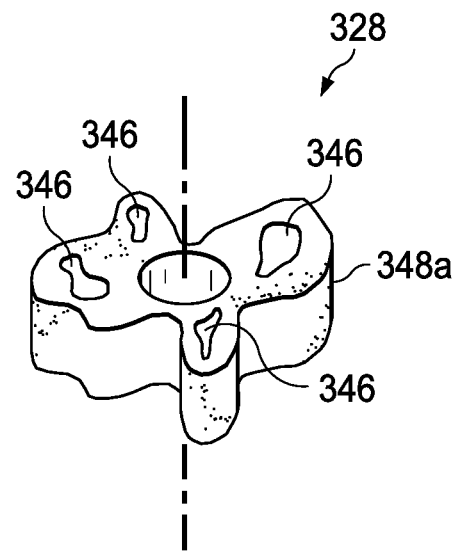
FIG. 12B is a perspective view of the temporary plug of FIG. 12A in a deteriorated state.

For example, referring to FIGS. 12A-12B, in some embodiments, a substrate of the temporary plug 328 may comprise a soluble material 348a. The soluble material 348a may be fluid impermeable and configured to deteriorate or dissolve after being exposed to moisture for a pre-determined time period. FIG. 12A depicts the temporary plug 328 in the serviceable state, and FIG. 12B depicts the temporary plug 328 in the deteriorated state in which at least a portion of the substrate material of the temporary plug 328 has deteriorated or dissolved. Deterioration or dissolution of the temporary plug 328 may create the fluid channels 346 through or around the temporary plug 328 such that the temporary plug 328 is not able to seal or preclude fluid communication through the vent 324.

Figure 13A:
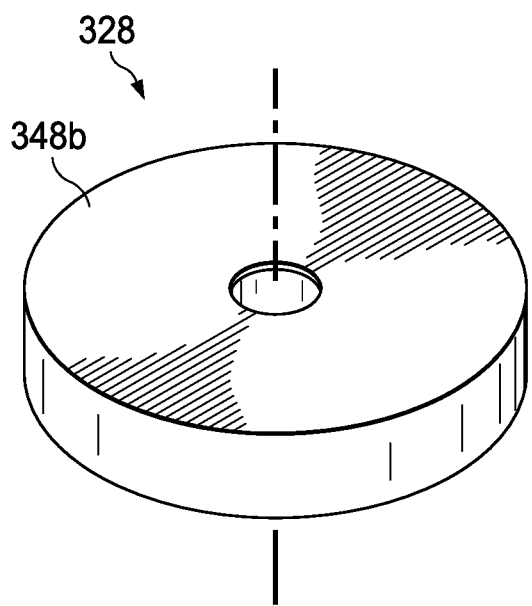
FIG. 13A is a perspective view of another illustrative example of a temporary plug in a serviceable state.
Figure 13B:
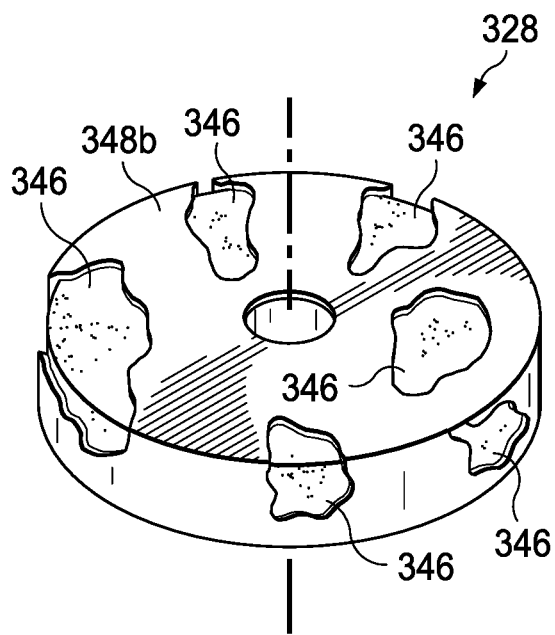
FIG. 13B is a perspective view of the temporary plug of FIG. 13A in a deteriorated state.

Referring to FIGS. 13A-13B, in some embodiments, the temporary plug 328 may comprise a fluid permeable sintered or porous material, such as a sintered polymer, that is coated or covered by a fluid impermeable soluble material 348b. The soluble material 348b may be configured to deteriorate or dissolve after being exposed to moisture for a pre-determined time period. FIG. 13A depicts the temporary plug 328 in the serviceable state, and FIG. 13B depicts the temporary plug 328 in the deteriorated state in which at least a portion of the soluble material 348b coating or covering the temporary plug 328 has deteriorated or dissolved. Deterioration or dissolution of the coating or covering of the soluble material 348b may open or define the fluid channels 346 through or around the temporary plug 328 such that the temporary plug 328 is not able to seal or preclude fluid communication through the vent 324. In such an embodiment, the fluid channels 346 may comprise openings formed in the soluble material 348b that permit fluid communication through interconnected pores in the temporary plug 328.

Figure 14A:
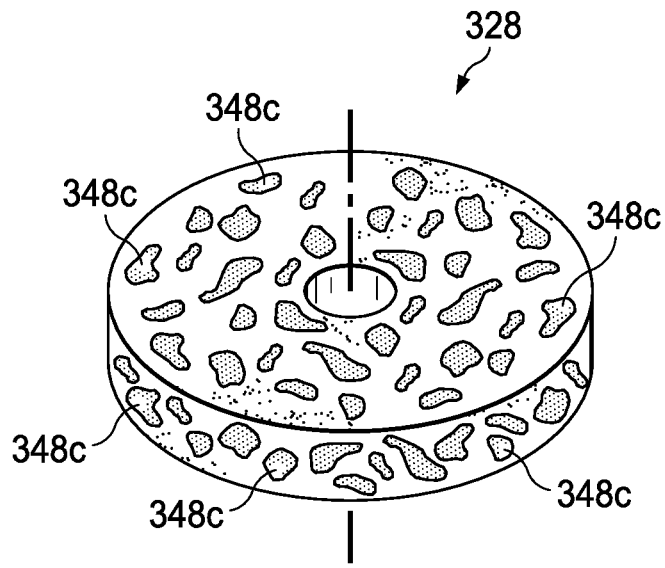
FIG. 14A is a perspective view of another illustrative example of a temporary plug in a serviceable state.
Figure 14B:
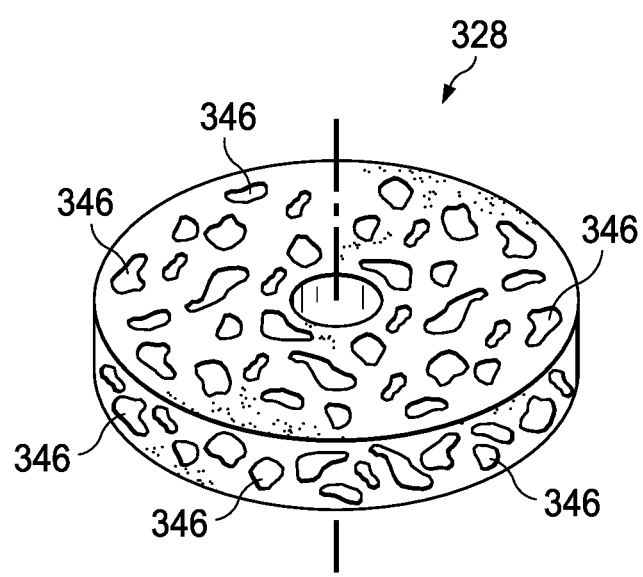
FIG. 14B is a perspective view of the temporary plug of FIG. 14A in a deteriorated state.

Referring to FIGS. 14A-14B, in some embodiments, the temporary plug 328 may comprise a sintered or porous material, such as a sintered polymer, that may include pores infiltrated or impregnated with a soluble material 348c. The soluble material 348c may be configured to deteriorate or dissolve after being exposed to moisture for a pre-determined time period. FIG. 14A depicts the temporary plug 328 in the serviceable state, and FIG. 14B depicts the temporary plug 328 in the deteriorated state in which at least a portion of the soluble material 348c infiltrated or impregnated in the temporary plug 328 has deteriorated or dissolved. Deterioration or dissolution of the soluble material 348c infiltrated or impregnated in the temporary plug 328 may open or define the fluid channels 346 in the form of interconnected pores, for example, through or around the temporary plug 328 such that the temporary plug 328 is not able to seal or preclude fluid communication through the vent 324.

In some embodiments, the temporary plug 328 may comprise, without limitation, any of the following materials or combination of materials: a sintered polymer; a casting; or a polymer or polymer film such as, without limitation, polyvinyl alcohol, polyvinylpyrrolidone, and polyvidone. In some embodiments, the soluble material 348a-c may comprise a polymer or polymer film, such as, without limitation: polyvinyl alcohol; polyvinylpyrrolidone; and polyvidone. Further, in some embodiments, temporary plug 328 may include a dye (not shown) configured to be released as the temporary plug 328 changes from the serviceable state to the deteriorated state. Release of the dye may provide an additional alert to a user or caretaker that the dressing 124 is full, or has reached a maximum fluid or liquid capacity, or otherwise requires replacement.

In operation, according to some illustrative embodiments, the interface manifold 120 may be disposed against or proximate to the tissue site 104. The dressing 124 may be applied over or covering the interface manifold 120 and the tissue site 104 to form the sealed space 174. For example, the base layer 132 may be applied covering the interface manifold 120 and tissue surrounding the tissue site 104. The materials described above for the base layer 132 may have a tackiness that may hold the dressing 124 initially in position. The tackiness may be such that if an adjustment is desired, the dressing 124 may be removed and reapplied. Once the dressing 124 is in the desired position, a force may be applied, such as hand pressure, on a side of the sealing member 140 facing outward or opposite the tissue site 104. The force applied to the sealing member 140 may cause at least some portion of the adhesive 136 to penetrate or extend through the plurality of apertures 160 and into contact with tissue surrounding the tissue site 104, such as the epidermis 106, to releaseably adhere the dressing 124 about the tissue site 104. In this manner, the configuration of the dressing 124 described herein may provide an effective and reliable seal against challenging anatomical surfaces, such as an elbow or heal, at and around the tissue site 104. Further, the dressing 124 may permit re-application or re-positioning to, for example, correct air leaks caused by creases and other discontinuities in the dressing 124 and the tissue site 104. The ability to rectify leaks may increase the reliability of the therapy and reduce power consumption.

As the dressing 124 comes into contact with fluid from the tissue site 104, the fluid may move through the apertures 160 toward the fluid management assembly 144, 244. The fluid management assembly 144, 244 may wick or otherwise move the fluid away from the tissue site 104, and through the interface manifold 120, if equipped. As described herein, the interface manifold 120 may be adapted to communicate fluid from the tissue site 104 rather than store the fluid. Thus, the fluid management assembly 144, 244 may be adapted to wick, pull, draw, or otherwise attract fluid from the tissue site 104 through the interface manifold 120. In the fluid management assembly 144, 244, the fluid may initially come into contact with the first dressing wicking layer 176, 276. The first dressing wicking layer 176, 276 may distribute the fluid laterally along the surface of the first dressing wicking layer 176, 276 for absorption or removal from the dressing 124. Similarly, fluid may come into contact with the second dressing wicking layer 180, 280 and may be distributed laterally along the surface of the second dressing wicking layer 180, 280 for absorption or removal from the dressing 124.

During initial or early stages of use when the dressing 124 is in a useable or serviceable state, the temporary plug 328 or valve 340 may provide a seal between the sealed space 174 and the atmosphere surrounding or exterior to the dressing 124. As the dressing 124 fills with fluid, components of the dressing 124, such as the absorbent 184, may become saturated with the fluid such that the fluid, for example, can no longer be held, stored, retained, or managed by the dressing 124. When the dressing 124 has reached such a saturation level, fluid in the dressing 124 may migrate or travel throughout the dressing 124 and the sealed space 174. In some embodiments, the fluid may travel or be drawn toward the inlet port 320 where reduced pressure is being applied to the dressing 124. As fluid continues to collect in the dressing 124 and the sealed space 174, the temporary plug 328, the valve 340, or components thereof may be exposed to the fluid. Fluid exposure or contact may cause the temporary plug 328 to change from the serviceable state to the deteriorated state. When the temporary plug 328 is in the deteriorated state, a seal may be broken between the sealed space 174 and the atmosphere exterior to the dressing 124, which may permit ambient air to enter the dressing 124 and the system 102. In an analogous manner described above, the valve 340 may be activated from the closed position to the open position as the valve 340 or components thereof are exposed to fluid in the dressing 124 or the sealed space 174.

Herein, the terms usable or serviceable may refer to the ability of a component of the system 102, such as the dressing 124 or the temporary plug 328, to perform as designed, as desired for a particular application, or in a clinically acceptable manner. Further, the term deteriorated may refer to a component of the system 102 that is no longer useable or serviceable or has otherwise reached the end of its life. Further, fluid may comprise gas, liquid, or vapor individually or in any combination. In some embodiments, the fluid may be vapor, such as moisture vapor, that permeates the at least one hydrophobic filter 336, such as the second hydrophobic filter 336b, associated with the temporary plug 328. In embodiments that use the at least one hydrophobic filter 336, liquid is precluded from passing through the hydrophobic filter 336. However, vapor is permitted to pass or permeate through the hydrophobic filter 336. Thus, the first hydrophobic filter 336a may be positioned as described to assist with preventing premature activation of the temporary plug 328 or the valve 340 due to fluid exposure occurring exterior to the dressing 124, which could occur, for example, in the event of a liquid spill on the exterior of the dressing 124 or through use of various cleaning agents on the exterior of the dressing 124.

As the temporary plug 328 changes from the serviceable state to the deteriorated state or the valve 340 changes from the closed position to the open position, ambient air begins to enter the system 102, and in particular, the sealed space 174 provided by the dressing 124. Since the sealed space 174 is open to the atmosphere in this configuration and the dressing 124 is no longer able to hold a pneumatic seal, a system failure or shutdown of the system 102 may occur to inform a user or caretaker that the dressing 124 is full, the dressing 124 has reached a maximum fluid or liquid saturation level, or that the dressing 124 requires replacement. For example, the reduced-pressure source 128 may attempt to counteract the increased air flow created by the broken seal. In embodiments where the reduced-pressure source 128 is a manual pump, the manual pump may not remain primed or ready for operation due at least in part to the inability of the system 102 to maintain a pneumatic seal, hold a vacuum, or otherwise maintain sufficient reduced pressure to continue therapeutic treatment. In embodiments where the reduced-pressure source 128 is a powered pump, the powered pump may run continuously or for periods outside of design parameters that may initiate a system alarm.

In some embodiments, a method for treating a tissue site, such as the tissue site 104, may include providing the dressing 124 and positioning the dressing 124 to form the sealed space 174 at the tissue site 104. Further, the method may include venting the sealed space 174 to ambient air exterior to the sealed space 174 when the dressing 124 requires replacement.

Further, in some embodiments, the method may include communicating a liquid to the dressing 124. Further, in some embodiments, the method may include applying reduced pressure to the sealed space 174 to draw a liquid from the tissue site 104 into the dressing 124. In some embodiments, the dressing 124 may require replacement when a liquid saturation level in the dressing 124 reaches a maximum capacity. In some embodiments, the dressing 124 may require replacement when the dressing 124 is substantially saturated with a liquid.

In some embodiments, venting the dressing 124 to ambient air may include providing fluid communication between the sealed space 174 and an atmosphere external to the sealed space 174. For example, in some embodiments, the dressing 124 may include the inlet port 320 and the vent 324. The inlet port 320 may be configured to communicate reduced pressure to the sealed space 174, and the vent 324 may be configured to provide fluid communication between the sealed space 174 and ambient air when the dressing 124 has reached a maximum liquid capacity. In some embodiments, venting the sealed space 174 may include deteriorating or dissolving at least a portion of the temporary plug 328, which may be positioned to temporarily preclude fluid communication through the vent 324. In some embodiments, deteriorating or dissolving the temporary plug 328 may include exposing the temporary plug 328 to moisture for a pre-determined time period. In some embodiments, the moisture may be vapor.

Although the subject matter of this disclosure has been provided by way of example in the context of certain illustrative, non-limiting embodiments, various changes, substitutions, permutations, and alterations can be made without departing from the scope of this disclosure as defined by the appended claims. Any feature described in connection to any one embodiment may also be applicable to any other embodiment. As such, the benefits and advantages described above may relate to one embodiment or may relate to several embodiments. Further, the steps of the methods described herein may be carried out in any suitable order, or simultaneously where appropriate.

What is claimed is:

1. A dressing configured to treat a tissue site, comprising:
   a sealing member configured to provide a sealed space at the tissue site;
   an inlet port configured to be in fluid communication with the sealed space;
   a vent configured to be in fluid communication between the sealed space and an atmosphere exterior to the sealed space; and
   a transformable plug comprising a soluble material configured to dissolve in the presence of moisture such that the transformable plug is configured to change from a serviceable state in which the transformable plug is fluid impermeable to a deteriorated state in which the transformable plug is fluid permeable after being exposed to moisture for a pre-determined time period, the transformable plug configured to preclude fluid communication through the vent in the serviceable state and to permit fluid communication through the vent in the deteriorated state.

2. The dressing of claim 1, wherein the sealing member comprises a liquid impermeable drape configured to cover the tissue site, and wherein the inlet port is configured to communicate reduced pressure from a reduced pressure source to the sealed space.

3. The dressing of claim 1, further comprising an absorbent configured to be positioned in the sealed space and between the tissue site and the sealing member, wherein the transformable plug is configured to change from the serviceable state to the deteriorated state in response to a liquid saturation level of the absorbent.

4. The dressing of claim 1, wherein the transformable plug is positioned in fluid communication between the inlet port and the vent.

5. The dressing of claim 1, wherein the transformable plug is positioned proximate to the inlet port.

6. The dressing of claim 1, wherein the transformable plug is positioned in the vent.

7. The dressing of claim 1, wherein the transformable plug is configured to seal the vent when in the serviceable state and to open the vent when in the deteriorated state.

8. The dressing of claim 1, wherein the transformable plug is configured to change from the serviceable state to the deteriorated state after being exposed to vapor for a pre-determined time period.

9. The dressing of claim 1, wherein the soluble material is configured to dissolve after being exposed to moisture for the pre-determined time period.

10. The dressing of claim 1, wherein the transformable plug comprises a sintered polymer.

11. The dressing of claim 1, wherein the transformable plug comprises a casting.

12. The dressing of claim 1, wherein the transformable plug comprises a polymer film.

13. The dressing of claim 1, wherein the transformable plug comprises a polymer film selected from the group consisting of: polyvinyl alcohol, polyvinylpyrrolidone, and polyvidone.

14. The dressing of claim 1, wherein the transformable plug comprises a material selected from the group consisting of: polyvinyl alcohol, polyvinylpyrrolidone, and polyvidone.

15. The dressing of claim 1, wherein the transformable plug comprises a dye configured to be released as the transformable plug changes from the serviceable state to the deteriorated state.

16. The dressing of claim 1, wherein the transformable plug comprises a sintered polymer coated with the soluble material.

17. The dressing of claim 1, wherein the transformable plug comprises a sintered polymer having pores infiltrated with the soluble material.

18. The dressing of claim 1, wherein the transformable plug is enclosed by at least one hydrophobic filter, and wherein the at least one hydrophobic filter is vapor permeable and liquid impermeable.

19. The dressing of claim 1, further comprising a first hydrophobic filter and a second hydrophobic filter, the first hydrophobic filter configured to be positioned in fluid communication between the atmosphere and the transformable plug, the second hydrophobic filter configured to be positioned in fluid communication between the transformable plug and the sealed space.

20. The dressing of claim 1, wherein the atmosphere is ambient air exterior to the sealed space.

21. The dressing of claim 1, wherein the inlet port and the vent are carried by a conduit interface configured to be coupled to the sealing member.

22. A conduit interface configured to fluidly communicate with a dressing for treating a tissue site, the conduit interface comprising:
a mounting surface and an exterior-facing surface positioned across from the mounting surface;
an internal cavity having an opening positioned proximate to the mounting surface;
an inlet port in fluid communication with the internal cavity through the exterior-facing surface;
a vent in fluid communication with the internal cavity through the exterior-facing surface; and
a temporary plug comprising a soluble material and being configured to temporarily preclude fluid communication through the vent when the temporary plug is in a serviceable state, wherein at least a portion of the soluble material is configured to deteriorate or dissolve to change the temporary plug from the serviceable state to a deteriorated state in which the temporary plug is fluid permeable and configured to permit fluid communication through the vent.

23. The conduit interface of claim 22, wherein the internal cavity is housed between the mounting surface and the exterior-facing surface.

24. The conduit interface of claim 22, wherein the mounting surface is configured to be coupled to the dressing such that the internal cavity is positioned in fluid communication with the dressing through the opening.

25. The conduit interface of claim 22, wherein the inlet port is configured to communicate reduced pressure from a reduced pressure source to the internal cavity.

26. The conduit interface of claim 22, wherein the inlet port and the vent are positioned on the exterior-facing surface.

27. The conduit interface of claim 22, wherein the temporary plug is positioned in a fluid passageway defined by the vent between the internal cavity and the exterior-facing surface.

28. The conduit interface of claim 22, wherein the temporary plug is positioned in the vent.

29. The conduit interface of claim 22, wherein the temporary plug is configured to seal the vent when in the serviceable state and to open the vent when in the deteriorated state.

30. The conduit interface of claim 22, wherein the temporary plug is configured to change from the serviceable state to the deteriorated state after being exposed to moisture for a pre-determined time period.

31. The conduit interface of claim 22, wherein the soluble material is configured to dissolve after being exposed to moisture for a pre-determined time period.

32. The conduit interface of claim 22, wherein the temporary plug is enclosed by at least one hydrophobic filter, and wherein the at least one hydrophobic filter is vapor permeable and liquid impermeable.

33. The conduit interface of claim 22, further comprising a first hydrophobic filter and a second hydrophobic filter, the first hydrophobic filter positioned covering the vent proximate the exterior-facing surface, the second hydrophobic filter positioned covering the opening proximate the mounting surface.

34. The conduit interface of claim 33, wherein the temporary plug is positioned between the first hydrophobic filter and the second hydrophobic filter.

35. A system for treating a tissue site, comprising:
a dressing, comprising:
a sealing member configured to cover the tissue site and to provide a sealed space between the sealing member and the tissue site,
an absorbent configured to be positioned in the sealed space and between the tissue site and the sealing member,
an inlet port configured to be in fluid communication with the sealed space,
a vent configured to be in fluid communication between the sealed space and an atmosphere exterior to the sealed space,
a transformable plug comprising a soluble material and being configured to change from a serviceable state in which the transformable plug is fluid impermeable to a deteriorated state in which the transformable plug is fluid permeable in response to a liquid saturation level of the absorbent, the transformable plug configured to preclude fluid communication through the vent in the serviceable state and to permit fluid communication through the vent in the deteriorated state, and at least one hydrophobic filter enclosing the transformable plug, the at least one hydrophobic filter being vapor permeable and liquid impermeable; and a reduced pressure source configured to be coupled in fluid communication with the dressing through the inlet port.

36. A method for treating a tissue site, comprising:
providing a dressing;
positioning the dressing to form a sealed space; and
venting the sealed space to ambient air exterior to the sealed space when the dressing requires replacement;
wherein venting the sealed space comprises exposing a temporary plug comprising a soluble material to moisture for a pre-determined time period in which the temporary plug changes from a fluid impermeable and serviceable state to a fluid permeable and deteriorated state.

37. The method of claim 36, further comprising communicating a liquid to the dressing, wherein the dressing requires replacement when a liquid saturation level in the dressing reaches a maximum capacity.

38. The method of claim 36, further comprising applying reduced pressure to the sealed space to draw a liquid from the tissue site into the dressing, wherein the dressing requires replacement when a liquid saturation level in the dressing reaches a maximum capacity.

39. The method of claim 36, wherein the dressing requires replacement when a liquid saturation level in the dressing reaches a maximum capacity.

40. The method of claim 36, wherein the dressing requires replacement when the dressing is substantially saturated with a liquid.

41. The method for treating a tissue site of claim 36, wherein venting the dressing to ambient air comprises providing fluid communication between the sealed space and an atmosphere external to the sealed space.

42. The method of claim 36, wherein the dressing comprises an inlet port and a vent, wherein the inlet port is configured to communicate reduced pressure to the sealed space, wherein the vent is configured to provide fluid communication between the sealed space and ambient air, and wherein venting the sealed space comprises dissolving at least a portion of the temporary plug positioned to temporarily preclude fluid communication through the vent.

43. The method of claim 36, wherein the moisture is vapor.

44. A dressing for treating a tissue site, comprising:
an inlet port configured to provide fluid communication to the dressing;
a valve configured to be activated from a closed position to an open position based on a liquid saturation level in the dressing, the valve configured to preclude fluid communication to ambient air external to the dressing in the closed position and to permit fluid communication to the ambient air in the open position, wherein the valve comprises a temporary plug including a soluble material configured to dissolve in the presence of moisture such that the temporary plug is fluid impermeable when the valve is in the closed position and fluid permeable when the valve is in the open position after the soluble material has been exposed to the liquid saturation level for a pre-determined time.

45. The dressing of claim 44, wherein the valve comprises:
a vent configured to provide fluid communication to the ambient air;
wherein the temporary plug is positioned to preclude fluid communication through the vent when the valve is in the closed position.

46. The dressing of claim 44, wherein the temporary plug is configured to dissolve when the valve is activated from the closed position to the open position.

47. The dressing of claim 44, further comprising a sealing member and an absorbent, wherein the sealing member is configured to provide a sealed space at the tissue site, wherein the absorbent is configured to be positioned in the sealed space between the sealing member and the tissue site, and wherein the valve is configured to be activated based on a liquid saturation level of the absorbent.

48. The dressing of claim 44, wherein the inlet port is configured to provide fluid communication between the sealed space and a reduced pressure source.

\* \* \* \* \*